United States Patent
Yoshida et al.

(10) Patent No.: US 9,365,587 B2
(45) Date of Patent: Jun. 14, 2016

(54) SYNTHESIS OF CARBAMOYLPYRIDONE HIV INTEGRASE INHIBITORS AND INTERMEDIATES

(71) Applicants: Shionogi & Co., Ltd., Osaka (JP); ViiV Healthcare Company, Research Traingle Park, NC (US)

(72) Inventors: Hiroshi Yoshida, Osaka (JP); Yoshiyuki Taoda, Osaka (JP); Brian Alvin Johns, Research Triangle Park, NC (US); Takashi Kawasuji, Osaka (JP); Daiki Nagamatsu, Osaka (JP)

(73) Assignees: SHIONOGI & CO., LTD., Osaka (JP); ViiV HEALTHCARE COMPANY, Research Triangle Park, NC (US)

( * ) Notice: Subject to any disclaimer, the term of this patent is extended or adjusted under 35 U.S.C. 154(b) by 0 days.

(21) Appl. No.: 14/936,987

(22) Filed: Nov. 10, 2015

(65) Prior Publication Data

US 2016/0060274 A1    Mar. 3, 2016

Related U.S. Application Data

(62) Division of application No. 14/272,823, filed on May 8, 2014, now Pat. No. 9,242,986, which is a division of application No. 14/096,191, filed on Dec. 4, 2013, now Pat. No. 8,754,214, which is a division of application No. 13/128,992, filed as application No. PCT/US2009/006422 on Dec. 8, 2009, now Pat. No. 8,624,023.

(60) Provisional application No. 61/193,634, filed on Dec. 11, 2008.

(51) Int. Cl.

| | |
|---|---|
| *C07D 498/14* | (2006.01) |
| *C07D 213/803* | (2006.01) |
| *C07D 213/81* | (2006.01) |
| *C07D 471/22* | (2006.01) |
| *A61K 31/351* | (2006.01) |
| *A61K 31/4412* | (2006.01) |
| *C07D 487/22* | (2006.01) |

(52) U.S. Cl.
CPC ............ *C07D 498/14* (2013.01); *A61K 31/351* (2013.01); *A61K 31/4412* (2013.01); *C07D 213/803* (2013.01); *C07D 213/81* (2013.01); *C07D 471/22* (2013.01); *C07D 487/22* (2013.01); *Y02P 20/55* (2015.11)

(58) Field of Classification Search
CPC ............ C07D 498/14; C07D 213/803; C07D 213/81; C07D 471/22
See application file for complete search history.

(56) References Cited

U.S. PATENT DOCUMENTS

| | | | |
|---|---|---|---|
| 4,524,149 | A | 6/1985 | Lesher et al. |
| 4,603,144 | A | 7/1986 | Campbell et al. |
| 4,735,964 | A | 4/1988 | Campbell et al. |
| 4,769,380 | A | 9/1988 | Jones et al. |
| 4,812,474 | A | 3/1989 | Campbell et al. |
| 5,688,815 | A | 11/1997 | Zbinden |
| 6,426,418 | B1 | 7/2002 | Tam et al. |
| 6,919,351 | B2 | 7/2005 | Anthony et al. |
| 7,211,572 | B2 | 5/2007 | Miyazaki et al. |
| 8,129,385 | B2 | 3/2012 | Johns et al. |
| 8,410,103 | B2 | 4/2013 | Johns et al. |
| 8,778,943 | B2 | 7/2014 | Johns et al. |
| 9,051,337 | B2 | 6/2015 | Johns et al. |
| 2001/0051732 | A1 | 12/2001 | Muraoka et al. |
| 2004/0167124 | A1 | 8/2004 | Chen et al. |

(Continued)

FOREIGN PATENT DOCUMENTS

| | | |
|---|---|---|
| CA | 2 379 370 | 9/2003 |
| EP | 0 171 814 | 2/1986 |

(Continued)

OTHER PUBLICATIONS

International Search Report issued Feb. 12, 2010 in International (PCT) Application No. PCT/US2009/006422 along with the Written Opinion.

J. R. Martinelli et al., "Convenience Method for the Preparation of Weinreb Amides via Pd-Catalyzed Aminocarbonylation of Aryl Bromides as Atmospheric Pressure", Organic Letters, vol. 8, No. 21, pp. 4843-4846, 2006.

J. Albaneze-Walker et al., "Improved Carbonylation of Heterocyclic Chlorides and Electronically Challenging Aryl Bromides", Organic Letters, vol. 6, No. 13, pp. 2097-2100, 2004.

(Continued)

*Primary Examiner* — Kahsay Habte

(74) *Attorney, Agent, or Firm* — Wenderoth, Lind & Ponack, L.L.P.

(57) ABSTRACT

The invention is a process for the preparation of a compound of the following formula (I):

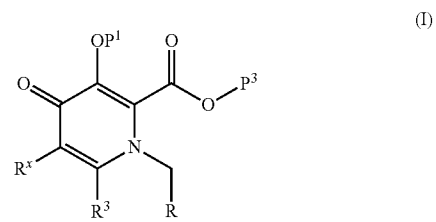

wherein R is —CHO, —CH(OH)$_2$ or —CH(OH)(OR$^4$); P$^1$ is H or a hydroxyl protecting group; P$^3$ is H or a carboxy protecting group; R$^3$ is H, halogen, hydroxy, optionally substituted lower alkyl, optionally substituted cycloalkyl, etc.; R$^x$ is H, halogen or R$^2$—X—NR$^1$—C(O)—; etc. as defined in the specification. The compounds are useful as intermediates in synthesizing compounds having HIV integrase inhibitory activity.

17 Claims, 7 Drawing Sheets

(56) References Cited

U.S. PATENT DOCUMENTS

| | | | |
|---|---|---|---|
| 2005/0054645 | A1 | 3/2005 | Miyazaki et al. |
| 2006/0019996 | A1 | 1/2006 | Tucci et al. |
| 2006/0116356 | A1 | 6/2006 | Cai et al. |
| 2006/0252944 | A1 | 11/2006 | Lantzsch et al. |
| 2007/0072831 | A1 | 3/2007 | Cai et al. |
| 2007/0249687 | A1 | 10/2007 | Yoshida |
| 2007/0270485 | A1 | 11/2007 | Wender et al. |
| 2008/0096886 | A1 | 4/2008 | Tam et al. |
| 2008/0161271 | A1 | 7/2008 | Yoshida et al. |
| 2008/0207562 | A1 | 8/2008 | Zander |
| 2009/0143356 | A1 | 6/2009 | Yoshida et al. |
| 2009/0318421 | A1 | 12/2009 | Johns et al. |
| 2011/0124598 | A1 | 5/2011 | Johns et al. |
| 2011/0183940 | A1 | 7/2011 | Johns et al. |
| 2011/0190236 | A1 | 8/2011 | Johns et al. |
| 2011/0263855 | A1 | 10/2011 | Johns et al. |
| 2011/0282055 | A1 | 11/2011 | Yoshida et al. |
| 2012/0022251 | A1 | 1/2012 | Sumino et al. |

FOREIGN PATENT DOCUMENTS

| | | |
|---|---|---|
| EP | 0 768 302 | 4/1997 |
| EP | 1 544 199 | 6/2005 |
| GB | 2280435 | 2/1995 |
| JP | 2006-342115 | 12/2006 |
| JP | 2007-509850 | 4/2007 |
| JP | 2008-540343 | 11/2008 |
| WO | 98/54138 | 12/1998 |
| WO | 2004/024078 A2 | 3/2004 |
| WO | 2004/024078 A3 | 3/2004 |
| WO | 2005/016927 | 2/2005 |
| WO | 2005/092099 | 10/2005 |
| WO | 2006/030807 | 3/2006 |
| WO | 2006/053429 | 5/2006 |
| WO | 2006/066414 | 6/2006 |
| WO | 2006/088173 | 8/2006 |
| WO | 2006/116764 | 11/2006 |
| WO | 2007/049675 | 5/2007 |
| WO | 2008-103277 | 8/2008 |
| WO | 2008/103277 | 8/2008 |
| WO | 2005/087766 | 9/2008 |
| WO | 2010/011812 | 1/2010 |
| WO | 2010/011814 | 1/2010 |
| WO | 2010/068253 | 6/2010 |
| WO | 2010/068262 | 6/2010 |
| WO | 2010/110409 | 9/2010 |
| WO | 2011/119566 | 9/2011 |
| WO | 2012/018065 | 2/2012 |

OTHER PUBLICATIONS

English translation of International Preliminary Report on Patentability and Written Opinion dated Jun. 14, 2011.
Extended European Search Report issued May 24, 2012 in EP application No. 9832232.4.
Johns et al., Copending U.S. Appl. No. 13/054,847, filed Apr. 8, 2011 published as U.S. Pat. No. 2011-0183940.
Sumino et al., Copending U.S. Appl. No. 13/260,063, filed Sep. 23, 2011 published as U.S. Pat. No. 2012-0022251.
Wang et al., Copending U.S. Appl. No. 13/636,237, filed Nov. 13, 2012 published as WO2011/119566.
Sumino et al., Copending U.S. Appl. No. 13/814,333, filed Feb. 5, 2013 published as WO 2012/018065.
M. Ghandi et al., "A Novel Method for the Synthesis of Formyl and Hydroxymethyl Derivatives *4H*-Pyran-4-One", Organic Preperations and Procedures International, vol. 34, No. 5, pp. 525-530, 2002.
Supplementary European Search Report issued Dec. 6, 2011 in EP Application No. 09800991.3.
J.D. Thomas et al., "Overcoming Steric Effects in the Coupling Reaction of Alkyloxycarbonyloxymethyl (AOCOM) Halides with Phenols: An Efficient Synthesis of AOCOM Phenolic Prodrugs", Tetrahedron Letters, vol. 48, No. 1, pp. 109-112, Nov. 30, 2006.
J.D. Thomas, "Improving the Topical Delivery of Phenol-Containing Drugs: An Alkylcarbonyloxymethyl and Alkyloxycarbonyloxymethyl Prodrug Approach", University of Florida, pp. 1-150, Dec. 31, 2006.
H. Yoshida et al., co-pending U.S. Appl. No. 13/128,457, filed Jul. 12, 2011, published as US 2011-0263855.
B. Johns et al., co-pending U.S. Appl. No. 13/054,633, filed Apr. 8, 2011, published as US 2011-0190236.
Supplementary European Search Report issued Jun. 13, 2012 in corresponding EP Application No. 09832226.6.
Y. K. Ko et al., "A New and Facile Synthesis of 2-Pyridones", Bull. Korean Chem. Soc., vol. 22, No. 2, pp. 234-236, 2001.
G. Chen et al., "Palladium-Catalyzed C-O Bond Formation: Direct Synthesis of Phenols and Aryl/Alkyl Ethers from Activated Aryl Halides", Tetrahedron Letters, vol. 48, pp. 473-476, 2007.
D. DeJohn et al., "Functionalization of Substituted 2(1H)- and 4(1H)-Pyridones. III. The Preparation of Substituted 6-Vinyl-1,2-Dihydro-2-Oxo- and 1,4-Dihydro-4-Oxo-3-Pyridinecarboxylic Acids Through the Chemistry of Pyridone Dianions", J. Heterocyclic Chem., vol. 20, pp. 1295-1302, Sep.-Oct. 1983.
J. C Hastings et al., "Anti-Influenza Virus Activities of 4-Substituted 2,4-Dioxobutanoic Acid Inhibitors", Antimicrobial Agents and Chemotherapy, vol. 40, No. 5, pp. 1304-1307, May 1996.
O. D. Hensens et al., "Isolation and Structure of Flutimide, A Novel Endonuclease Inhibitor of Influenza Virus", Tetrahedron Letters, vol. 36, No. 12, pp. 2005-2008, 1995.
B. W. McCleland et al., "Comparison N,N1-Diarysquaramides and N,N1-Diarylureas as Antagonists of the CXCR2 Chemokine Receptor", Bioorganic & Medicinal Chemisty Letters, vol. 17, pp. 1713-1717, 2007.
S. W. McCombie et al., "Generation and in Situ Acylation of Enaminone Anions: A Convenient Synthesis of 3-Carbethoxy-4(1H)-Pyridinones and 4-Pyrones and Related Compounds", J. Org. Chem., vol. 56, No. 16, pp. 4963-4967, 1991.
K. E. B. Parkes et al., "Use of a Pharmacophore Model to Discover a New Class of Influenza Endonuclease Inhibitors", J. Med. Chem., vol. 46, No. 7, pp. 1153-1164, 2003.
W. J. Ross et al., "The Synthesis and Rearrangement of Epoxypyrones", Tetrahedron Letters, vol. 22, No. 23, pp. 2207-2208, 1981.
S. B. Singh, "Total Synthesis of Flutimide, A Novel Endonuclease Inhibitor of Influenza Virus", Tetrahedron Letters, vol. 36, No. 12, pp. 2009-2012, 1995.
J. Tomassini et al., "Inhibition of Cap (m7GpppXm)-Dependent Endonuclease of Influenza Virus by 4-Substituted 2,4-Dioxobutanoic Acid Compounds", Antimicrobial Agents and Chemotherapy, vol. 38, No. 12, pp. 2827-2837, Dec. 1994.
J. S. Wai et al., "Dihydroxypyridopyrazine-1,6-Dione HIV-1 Integrase Inhibitors", Bioorganic & Medicinal Chemistry Letters, vol. 17, pp. 5595-5599, 2007.
L. L. Woods et al., "Reactions of Pyrones Catalyzed by Trifluoroacetic Acid", J. Org. Chem., pp. 1052-1053, Jun. 1960.
S. Kukolja et al., "Studies on 4-Pyrones and 4-Pyridones. II. The Preparation and Rearrangement of 3-Allyloxy-4-Pyrone", Croatica Chemica Acta, vol. 33, pp. 229-233, 1961.

SYNTHESIS OF CARBAMOYLPYRIDONE HIV INTEGRASE INHIBITORS AND INTERMEDIATES

FIELD OF THE INVENTION

The present invention comprises modifications of known processes for synthesizing compounds having HIV integrase inhibitory activity.

BACKGROUND OF THE INVENTION

WO 2006/116764 published 2 Nov. 2006, incorporated by reference in its entirety, describes various compounds and detailed synthetic schemes for their preparation. In particular, a reaction sequence is depicted at page 79 thereof wherein 3-benzyloxy-2-methyl-1H-pyridine-4-one of formula 3 is there brominated to the bromopyridine 4 there, which is then reacted with methanol and carbon monoxide to yield the nicotinic acid methyl ester 5 there which is after several steps reacted with a benzylamine to create the amide side chain-containing pyridine 10. Thus, the amide sidechain is in place before creation of the $Z^1Z^2$ ring of the final product formula (I) therein in the reaction depicted at page 80 from 16 to 17-1.

A second reaction sequence is depicted at page 113 of WO 2006/116764 wherein a pyrrolidine compound 102 is allowed to condense into a tricyclic compound 103 which is then brominated to yield the bromine compound 104 which is then reacted with a benzylamine to create the amide side chain-containing tricyclic compound 105 therein. Thus, the bromination takes place after creation of the $Z^1Z^2$ ring of the final product of formula (I) therein.

N-Methoxy-N-methyl amides may be prepared by Pd catalyzed aminocarbonylation of aryl bromides as described by J. R. Martinelli et al in Organic Letters, Vol. 8, No. 21, pages 4843-4846 (2006). Bromoanilines and bromoanisoles are converted to esters as described by J. Albaneze-Walker et al in Organic Letters, Vol. 6, No. 13, pages 2097-2100 (2004).

SUMMARY OF THE INVENTION

Processes are provided which utilize an early bromination step in the construction of compounds useful as having HIV integrase inhibitory activity as set forth in WO 2006/116764. The bromination provides the leaving group for attachment of an amide side chain on a pyridone ring.

DETAILED DESCRIPTION OF THE INVENTION

Figure 1:
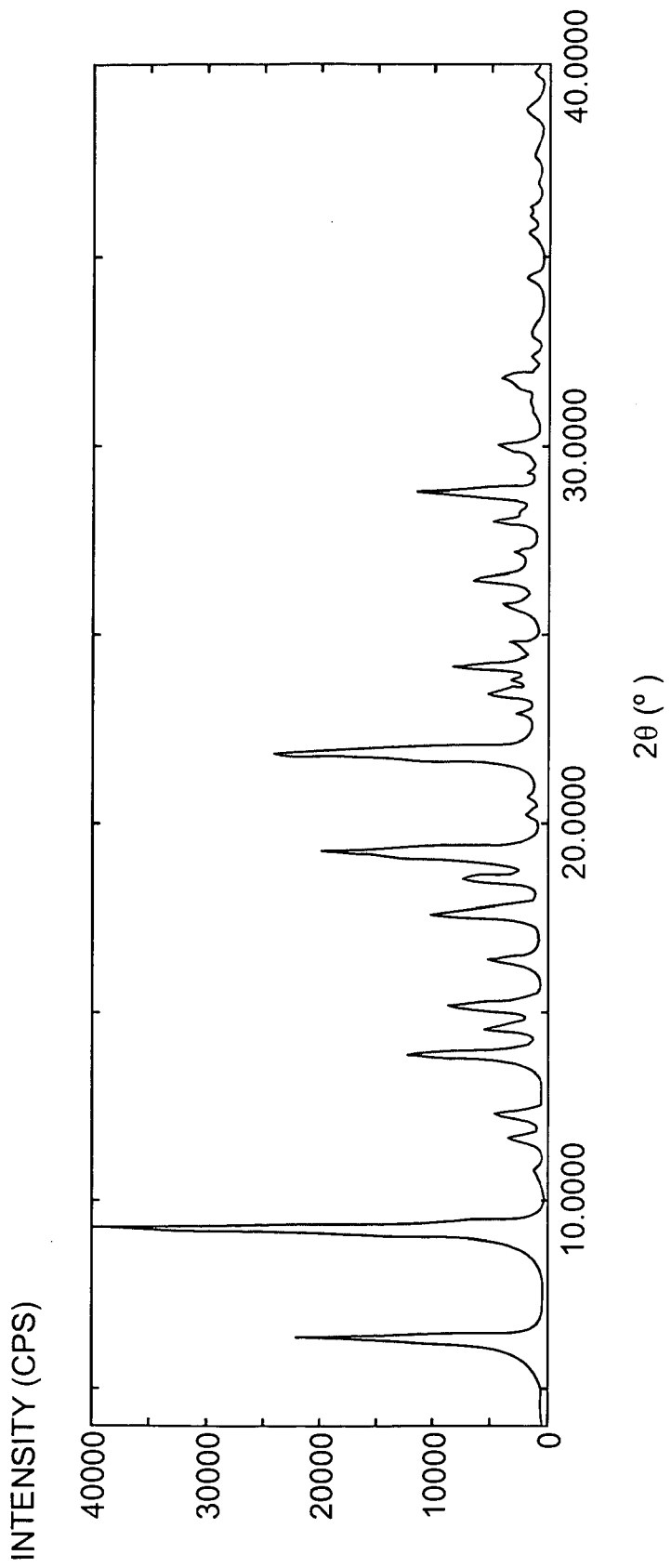
FIG. 1 shows an X-ray power diffraction pattern of a crystal of compound 13.

A process is provided within a synthesis of a pyridone compound of the following formula (AA), (BB) or (CC):

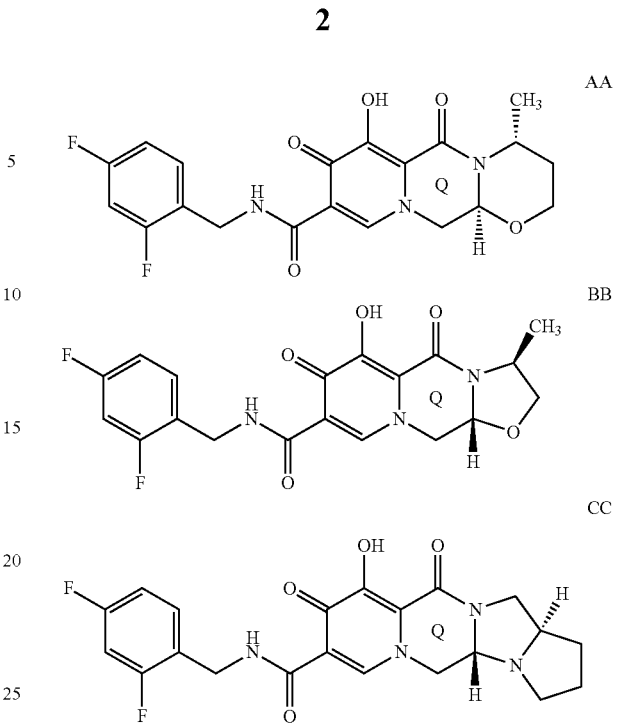

comprising the steps of:

P-1) brominating a compound of the following formula (I-I) to produce a bromine compound of the following formula (II-II):

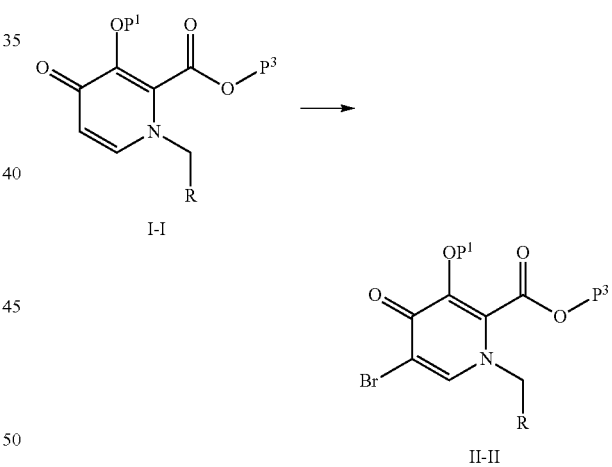

wherein

R is —CHO, —CH(OH)$_2$, —CH(OH)(OR$^4$), —CH(OH)—CH$_2$OH or —CH(OR$^5$)(OR$^6$);

P$^1$ is H or a hydroxyl protecting group;

P$^3$ is H or a carboxy protecting group;

R$^4$ is lower alkyl;

R$^5$ and R$^6$ are independently lower alkyl or R$^5$ and R$^6$ can be lower alkyl and joined to form a 5-, 6-, or 7-membered ring, and P-2) creating the 2,4-di-fluorophenyl-CH$_2$—NH—C(O)— sidechain with the reactants 2,4-di-fluorophenyl-CH$_2$—NH$_2$ and carbon monoxide.

The term "lower alkyl", alone or in combination with any other term, refers to a straight-chain or branched-chain saturated aliphatic hydrocarbon radical containing 1 to 6 carbon atoms. Examples of alkyl radicals include, but are not limited to, methyl, ethyl, n-propyl, isopropyl, n-butyl, isobutyl, sec-butyl, tert-butyl, pentyl, isoamyl, n-hexyl and the like.

The term "lower cycloalkyl" refers to a saturated or partially saturated carbocyclic ring composed of 3-6 carbons in any chemically stable configuration. Examples of suitable carbocyclic groups include cyclopropyl, cyclobutyl, cyclopentyl, cyclohexyl, and cyclohexenyl.

The term "lower alkenyl," alone or in combination with any other term, refers to a straight-chain or branched-chain alkyl group with one or two carbon-carbon double bonds. Examples of alkenyl radicals include, but are not limited to, ethenyl, propenyl, isopropenyl, butenyl, isobutenyl, pentenyl, hexenyl, hexadienyl and the like.

The term "lower alkylene" refers to a straight or branched chain divalent hydrocarbon radical, preferably having from one to six carbon atoms, unless otherwise defined. Examples of "alkylene" as used herein include, but are not limited to, methylene, ethylene, propylene, butylene, isobutylene and the like.

The term "lower alkenylene" refers to a straight or branched chain divalent hydrocarbon radical, one or two carbon-carbon double bonds.

The term "lower alkoxy" refers to an alkyl ether radical, wherein the term "alkyl" is defined above. Examples of suitable alkyl ether radicals include, but are not limited to, methoxy, ethoxy, n-propoxy, isopropoxy, n-butoxy, isobutoxy, sec-butoxy, tert-butoxy and the like.

The term "halogen" refers fluorine (F), chlorine (CI), bromine (Br), or iodine (I).

The term "aryl" alone or in combination with any other term, refers to a carbocyclic aromatic moiety (such as phenyl or naphthyl) containing 6 carbon atoms, and more preferably from 6-10 carbon atoms. Examples of aryl radicals include, but are not limited to, phenyl, naphthyl, indenyl, azulenyl, fluorenyl, anthracenyl, phenanthrenyl, tetrahydronaphthyl, indanyl, phenanthridinyl and the like. Unless otherwise indicated, the term "aryl" also includes each possible positional isomer of an aromatic hydrocarbon radical, such as in 1-naphthyl, 2-naphthyl, 5-tetrahydronaphthyl, 6-tetrahydronaphthyl, 1-phenanthridinyl, 2-phenanthridinyl, 3-phenanthridinyl, 4-phenanthridinyl, 7-phenanthridinyl, 8-phenanthridinyl, 9-phenanthridinyl and 10-phenanthridinyl. Examples of aryl radicals include, but are not limited to, phenyl, naphthyl, indenyl, azulenyl, fluorenyl, anthracenyl, phenanthrenyl, tetrahydronaphthyl, indanyl, phenanthridinyl and the like. The term "aralkyl" refers to an alkyl group substituted by an aryl. Examples of aralkyl groups include, but are not limited to, benzyl and phenethyl.

The term "heterocyclic group," and "heterocycle" as used herein, refer to a 3- to 7-membered monocyclic heterocyclic ring or 8- to 11-membered bicyclic heterocyclic ring system any ring of which is either saturated, partially saturated or unsaturated, and which may be optionally benzofused if monocyclic. Each heterocycle consists of one or more carbon atoms and from one to four heteroatoms selected from the group consisting of N, O and S, and wherein the nitrogen and sulfur heteroatoms may optionally be oxidized, and the nitrogen atom may optionally be quaternized, and including any bicyclic group in which any of the above-defined heterocyclic rings is fused to a benzene ring. The heterocyclic ring may be attached at any carbon or heteroatom, provided that the attachment results in the creation of a stable structure. Preferred heterocycles include 5-7 membered monocyclic heterocycles and 8-10 membered bicyclic heterocycles. When the heterocyclic ring has substituents, it is understood that the substituents may be attached to any atom in the ring, whether a heteroatom or a carbon atom, provided that a stable chemical structure results. "Heteroaromatics" or "heteroaryl" are included within the heterocycles as defined above and generally refers to a heterocycle in which the ring system is an aromatic monocyclic or polycyclic ring radical containing five to twenty carbon atoms, preferably five to ten carbon atoms, in which one or more ring carbons, preferably one to four, are each replaced by a heteroatom such as N, O, S and P. Preferred heteroaryl groups include 5-6 membered monocyclic heteroaryls and 8-10 membered bicyclic heteroaryls. Also included within the scope of the term "heterocycle, "heterocyclic" or "heterocyclyl" is a group in which a non-aromatic heteroatom-containing ring is fused to one or more aromatic rings, such as in an indolinyl, chromanyl, phenanthridinyl or tetrahydro-quinolinyl, where the radical or point of attachment is on the non-aromatic heteroatom-containing ring. Unless otherwise indicated, the term "heterocycle, "heterocyclic" or "heterocyclyl" also included each possible positional isomer of a heterocyclic radical, such as in 1-indolinyl, 2-indolinyl, 3-indolinyl. Examples of heterocycles include imidazolyl, imidazolinoyl, imidazolidinyl, quinolyl, isoquinolyl, indolyl, indazolyl, indazolinolyl, perhydropyridazyl, pyridazyl; pyridyl, pyrrolyl, pyrrolinyl, pyrrolidinyl, pyrazolyl, pyrazinyl, quinoxolyl, piperidinyl, pyranyl, pyrazolinyl, piperazinyl, pyrimidinyl, pyridazinyl, morpholinyl, thiamorpholinyl, furyl, thienyl, triazolyl, thiazolyl, carbolinyl, tetrazolyl, thiazolidinyl, benzofuranoyl, thiamorpholinyl sulfone, oxazolyl, oxadiazolyl, benzoxazolyl, oxopiperidinyl, oxopyrrolidinyl, oxoazepinyl, azepinyl, isoxozolyl, isothiazolyl, furazanyl, tetrahydropyranyl, tetrahydrofuranyl, thiazolyl, thiadiazoyl, dioxolyl, dioxinyl, oxathiolyl, benzodioxolyl, dithiolyl, thiophenyl, tetrahydrothiophenyl, sulfolanyl, dioxanyl, dioxolanyl, tetahydrofurodihydrofuranyl, tetrahydropyranodihydrofuranyl, dihydropyranyl, tetradyrofurofuranyl and tetrahydropyranofuranyl.

Optional substituents are hydroxy, halogen, amino and lower alkyl:

Protecting groups may be selected from groups known to those skilled in the art, including protecting groups disclosed in Greene, Theodora W.; Wuts, Peter G. M. Protective Groups in Organic Synthesis. 2nd Ed. (1991), 473 pp. or Kocienski, Philip J. Protecting Groups. 3rd Ed. 2005, (2005), 679 pp.

The pyridone ring depicted in (I-I) and (II-II), ie to which the —OP$^1$ is directly attached, becomes in AA, BB and CC the ring shown next to the Q ring as follows:

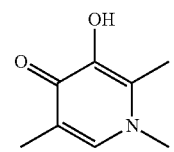

Thus, the step P-2) can be carried out before or after creation of the Q ring, such steps for the creation of the Q ring being described herein and in WO 2006/1116764.

The present invention features a process as described above, wherein said step P-2) is carried out before creation of the Q ring and wherein said pyridone compound is of the formula AA or formula BB or formula CC.

The present invention features a process as described above, wherein said step P-2) is carried out after creation of the Q ring and wherein said pyridone compound is of the formula AA or formula BB or formula CC.

The present invention features a process as described above, wherein the pyridone compound is of the formula AA.

The present invention features a process as described above, wherein the pyridone compound is of the formula BB.

The present invention features a process as described above, wherein the pyridone compound is of the formula CC.

Also part of the present invention are novel intermediates such as those of the following formula (DD) below:

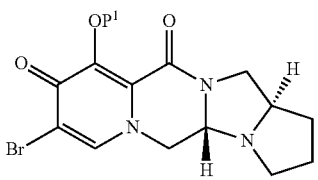

DD wherein $P^1$ is as described above, particularly benzyl.

A process is provided for the preparation of a pyridone compound of the following formula (AA), (BB) or (CC):

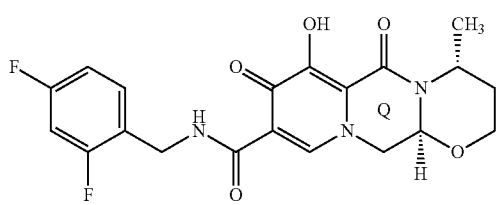

AA

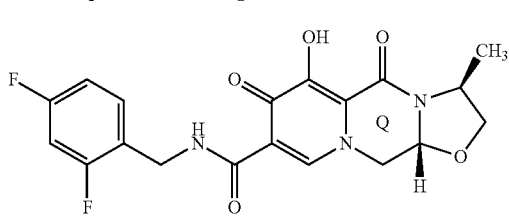

BB

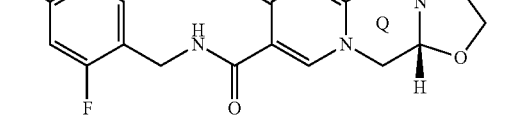

CC comprising the steps of:

P-1) brominating a compound of the following formula (I-I) to produce a bromine compound of the following formula (II-II):

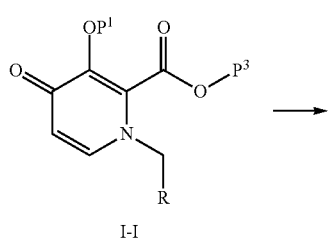

I-I

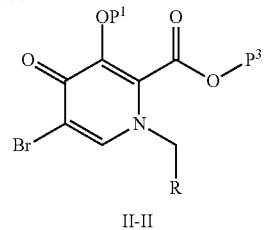

II-II wherein
R is —CHO; —CH(OH)$_2$, —CH(OH)(OR$^4$), —CH(OH)—CH$_2$OH or —CH(OR$^5$)(OR$^6$);
$P^1$ is H or a hydroxyl protecting group;
$P^3$ is H or a carboxy protecting group;
$R^4$ is lower alkyl;
$R^5$ and $R^6$ are independently lower alkyl or $R^5$ and $R^6$ can be lower alkyl and joined to form a 5-, 6-, or 7-membered ring, P-2) creating the 2,4-di-fluorophenyl-CH$_2$—NH—C(O)— sidechain with the reactants 2,4-di-fluorophenyl-CH$_2$—NH$_2$ and carbon monoxide to form a compound of formula

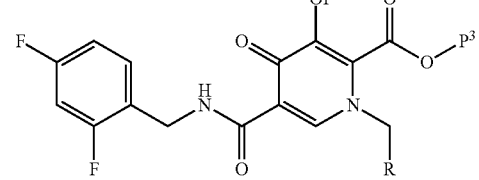

III-III

P-3) condensing and debenzylating a compound of formula III-III to form a compound of formula AA, BB, or CC.

The present invention also features processes as described above wherein $P^1$ is benzyl; $P^3$ is methyl; and R is —CHO, —CH(OH)(OR$^4$), —CH(OR$^5$)(OR$^5$) wherein $R^4$ and $R^5$ are lower alkyl.

There is also described herein the process for the preparation of a compound of the following formula (I):

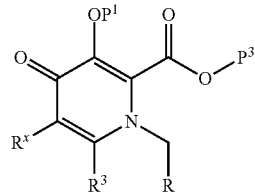

(I)

wherein
R is —CHO, —CH(OH)$_2$ or —CH(OH)(OR$^4$);
$P^1$ is H or a hydroxyl protecting group;
$P^3$ is H or a carboxy protecting group;
$R^3$ is H, halogen, hydroxy, optionally substituted lower alkyl, optionally substituted cycloalkyl, optionally substituted lower alkenyl, optionally substituted lower alkoxy, optionally substituted lower alkenyloxy, optionally substituted aryl, optionally substituted aryloxy, optionally substituted heterocyclic group, optionally substituted heterocycleoxy and optionally substituted amino;

$R^4$ is lower alkyl;

$R^x$ is H, halo or $R^2$—X—NR'—C(O)—;

$R^2$ is optionally substituted aryl;

X is a single bond, a heteroatom group selected from O, S, SO, $SO_2$, and NH or loweralkylene or lower alkenylene wherein each may be intervened by the heteroatom; and $R^1$ is H or lower alkyl, which comprises the steps of:

i) reacting a compound of formula (II):

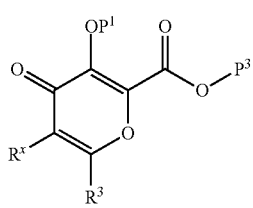
(II)

with an amine of formula (III) or (IV):

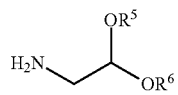
(III)

wherein $R^5$ and $R^6$ are independently lower alkyl or $R^5$ and $R^6$ can be alkyl and joined to form a 5-, 6-, or 7-membered ring,

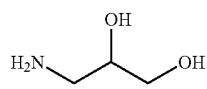
(IV)

to produce an intermediate of formula (V) or (VI), respectively:

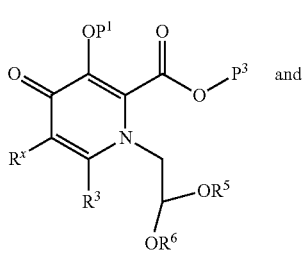
(V)

and

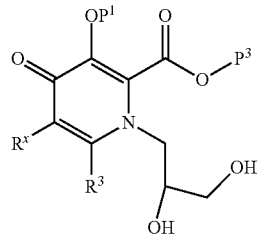
(VI)

ii) refunctionalizing (V) or (VI) to produce (I).

Specific compounds used in the processes include those of the following formulae (IIa), (VIa), (VIb) and (Ia) utilized in Examples which follow:

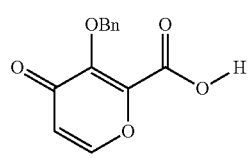
(IIa)

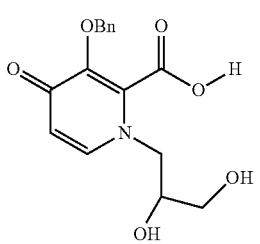
(IVa)

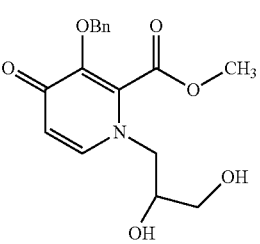
(VIb)

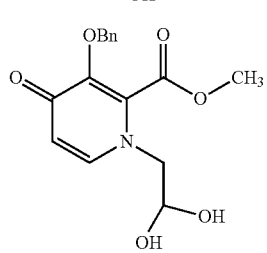
(Ia)

The product (Ia) of a synthetic sequence can be condensed with an amine, eg of the formula $H_2NCH_2CH_2CH_2OH$, brominated if $R^x$ is H, carbonylated and amidated and finally, debenzylated to yield a compound of WO 2006/116764 designated (I-7) at page 240 wherein $(R)_m$ is 4-F and $R^a$ is H. Alternatively, such a compound may be synthesized by starting with (I) where $R^x$ is p-F-phenyl-$CH_2$—NH—C(O)—, $R^3$ is H, $P^1$ is benzyl (Bn) and $P^3$ is a carboxy protecting group.

In more detail, step i) can be carried out in a protic or aprotic solvent such as EtOH, THF or DMF at a temperature of about 50-150° C. for about 1-10 hours.

In more detail, step ii) can be carried out for the diol starting material (VI) with an oxidizing agent such as $NaIO_4$, $RuO_4$ or Pb(OAc)$_4$ in a solvent such as H$_2$O, MeOH or CH$_3$CN at ambient temperature for one or more hours. For the acetal type starting material such as (V), reaction may be in an acid such as HCl, CF$_3$COOH or HCOH optionally with heating.

Step ii) can also involve refunctionalization at the R$^x$ position, eg R$^x$=H to R$^x$=Br optionally with further refunctionalization to R$^x$=R$^2$—X—NR'—C(O)—. Step ii) can also involve refunctionalization of P$^3$, eg P$^3$=H to P$^3$=Me.

In more detail, step P-1) can be carried out by treating a compound of formula I-I with a bromine source including but not limited to N-bromosuccinimide or bromine in a solvent such as N,N-dimethyl formamide, THF or acetic acid and the like. This transformation can be run particularly at a temperature of –10° C. to 50° C. to produce a compound of formula II-II.

In more detail, step P-2) can be carried out by treating a compound of formula II-II with 2,4-difluorophenyl-CH$_2$—NH$_2$, carbon monoxide, a suitable base and palladium (0) source and optionally an appropriate ligand in an inert solvent optionally with heating. The carbon monoxide can be at atmospheric pressure (14.7 psi) or at elevated pressure particularly in the range of up to 60 psi but in some cases higher pressures may be required. Bases include but are not limited to tertiary amine bases such as diisopropylethylamine and triethylamine and the like. Inorganic bases such as potassium acetate and potassium phosphate are also bases of significance. Suitable sources of Pd (0) include but are not limited to tetrakis triphenylphosphine palladium (0). In some cases a Pd (II) precursor can be used to generate Pd (0) in situ. Suitable Pd (II) precursors include but are not limited to Pd(OAc)$_2$, Pd(OCOCF$_3$)$_2$ and ligands include Xantphos, diphenylphosphinoferrocene (dppf), triphenylphosphine and the like. Solvents include N,N-dimethyl formamide, THF, toluene, DMSO and the like. Heating the mixture is optionally used in the range from ambient to 150° C.

The present invention also features crystalline forms of a compound of formula AA (Compound 13, Example 1) salt and a hydrate thereof. The present invention features:

(1) A salt or a hydrate thereof of a compound of formula AA:

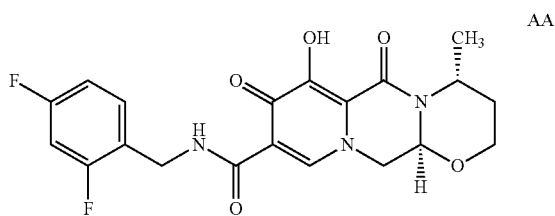 [SMILES: C[C@@H]1CCO[C@H]2Cn3cc(C(=O)NCc4ccc(F)cc4F)c(=O)c(O)c3C(=O)N12]

(2) A crystal form of a sodium salt or a hydrate thereof of a compound of formula AA:

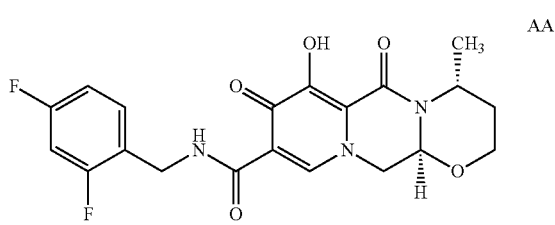 [SMILES: C[C@@H]1CCO[C@H]2Cn3cc(C(=O)NCc4ccc(F)cc4F)c(=O)c(O)c3C(=O)N12]

(3) A crystal form of (2) having one or more physical properties selected from the group consisting of (i) and (ii):
(i) having characteristic diffraction peaks at 6.4°±0.2°, 9.2°±0.2°, 13.8°±0.2°, 19.2°±0.2° and 21.8°±0.2° degrees two-theta in an X-ray powder diffraction pattern; and
(ii) having characteristic infrared absorption spectra at 1641 cm$^{-1}$±2 cm$^{-1}$, 1536 cm$^{-1}$±2 cm$^{-1}$, 1503 cm$^{-1}$±2 cm$^{-1}$ and 1424 cm$^{-1}$±2 cm$^{-1}$.

(4) A crystal form of (2) having characteristic diffraction peaks at 6.4°±0.2°, 9.2°±0.2°, 13.8°±0.2°, 19.2°±0.2° and 21.8°±0.2° degrees two-theta in an X-ray powder diffraction pattern.

(5) A crystal form of (2) having characteristic diffraction peaks at 6.4°±0.2°, 9.2°±0.2°, 13.8°±0.2°, 14.6°±0.2°, 15.2°±0.2°, 17.6°±0.2°, 19.2°±0.2°, 21.8°±0.2°, 24.1°±0.2° and 28.7°±0.0.2° degrees two-theta in an X-ray powder diffraction pattern.

(6) A crystal form of (2) having characteristic infrared absorption spectra at 1641 cm$^{-1}$±2 cm$^{-1}$, 1536 cm$^{-1}$±2 cm$^{-1}$, 1503 cm$^{-1}$±2 cm$^{-1}$ and 1424 cm$^{-1}$±2 cm$^{-1}$.

(7) A crystal form of (2) having characteristic infrared absorption spectra at 1641 cm$^{-1}$±2 cm$^{-1}$, 1536 cm$^{-1}$±2 cm$^{-1}$, 1503 cm$^{-1}$±2 cm$^{-1}$, 1424 cm$^{-1}$±2 cm$^{-1}$, 1282 cm$^{-1}$±2 cm$^{-1}$, 1258 cm$^{-1}$±2 cm$^{-1}$, 1093 cm$^{-1}$±2 cm$^{-1}$ and 1069 cm$^{-1}$±2 cm$^-$.

Figure 2:
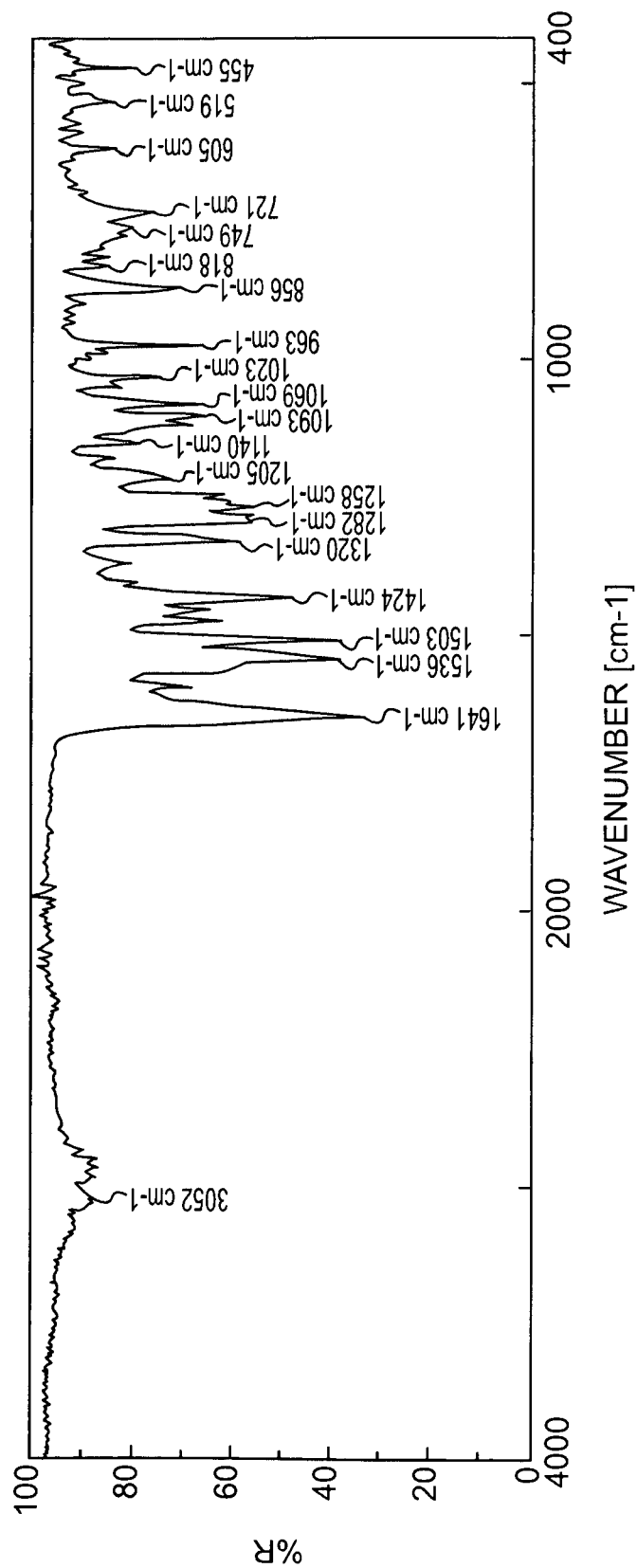
FIG. 2 shows an infrared absorption spectra of a crystal of compound 13.
Figure 3:
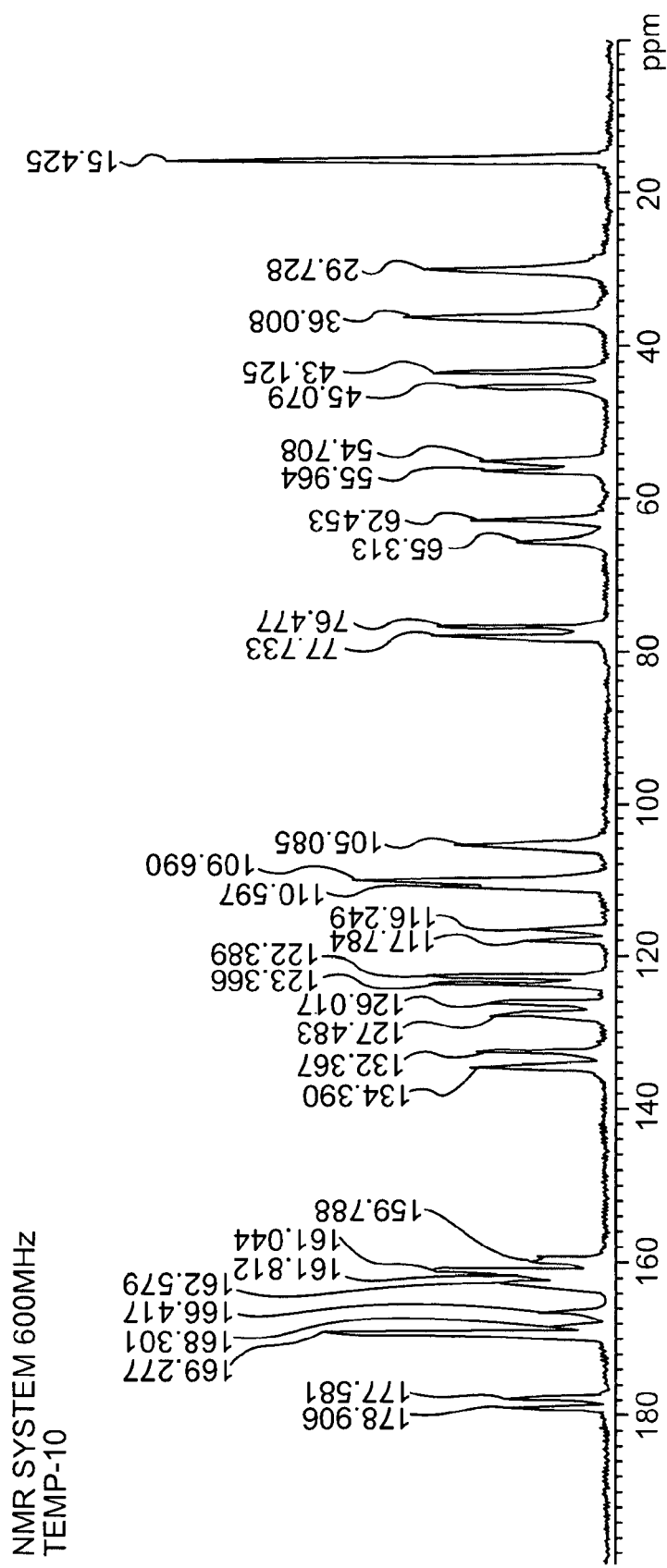
FIG. 3 shows a solid state $^{13}C$-NMR spectra of a crystal of compound 13.

(8) A crystal form of (2) having one or more spectra selected from the group consisting of (a) to (c):
(a) X-ray powder diffraction pattern substantially as shown in FIG. 1;
(b) Infrared absorption spectra substantially as shown in FIG. 2; and
(c) Solid state $^{13}$C-NMR spectra substantially as shown in FIG. 3.

(9) A crystal form of (2) having one or more physical properties selected from the group consisting of (iii) and (iv):
(iii) having characteristic diffraction peaks at 8.0°±0.2°, 9.3°±0.2°, 11.3°±0.2°, 16.0°±0.2°, and 22.8°±0.2° degrees two-theta in an X-ray powder diffraction pattern; and
(iv) having characteristic infrared absorption spectra at 1637 cm$^{-1}$±2 cm$^{-1}$, 1536 cm$^{-1}$±2 cm$^{-1}$, 1501 cm$^{-1}$±2 cm$^{-1}$ and 1422 cm$^{-1}$±2 cm$^{-1}$.

(10) A crystal form of (2) having characteristic diffraction peaks at 8.0°±0.2°, 9.3°±0.2°, 11.3°±0.2°, 16.0°±0.2° and 22.8°±0.2° degrees two-theta in an X-ray powder diffraction pattern.

(11) A crystal form of (2) having characteristic diffraction peaks at 8.0°±0.2°, 9.3°±0.2°, 11.3°±0.2°, 15.4°±0.2°, 16.0°±0.2°, 18.7°±0.2°, 19.1°±0.2°, 19.8°±0.2°, 22.8°±0.2° and 26.8°±0.2° degrees two-theta in an X-ray powder diffraction pattern.

(12) A crystal form of (2) having characteristic infrared absorption spectra at 1637 cm$^{-1}$±2 cm$^{-1}$, 1536 cm$^{-1}$±2 cm$^{-1}$, 1501 cm$^{-1}$±2 cm$^{-1}$ and 1422 cm$^{-1}$±2 cm$^{-1}$.

(13) A crystal form of (2) having characteristic infrared absorption spectra at 1637 cm$^{-1}$±2 cm$^{-1}$, 1536 cm$^{-1}$±2 cm$^{-1}$, 1501 cm$^{-1}$±2 cm$^{-1}$, 1422 cm$^{-1}$±2 cm$^{-1}$, 1277 cm$^{-1}$±2 cm$^{-1}$, 1258 cm$^{-1}$±2 cm$^{-1}$, 1093 cm$^{-1}$±2 cm$^{-1}$ and 1069 cm$^{-1}$±2 cm$^{-1}$.

Figure 4:
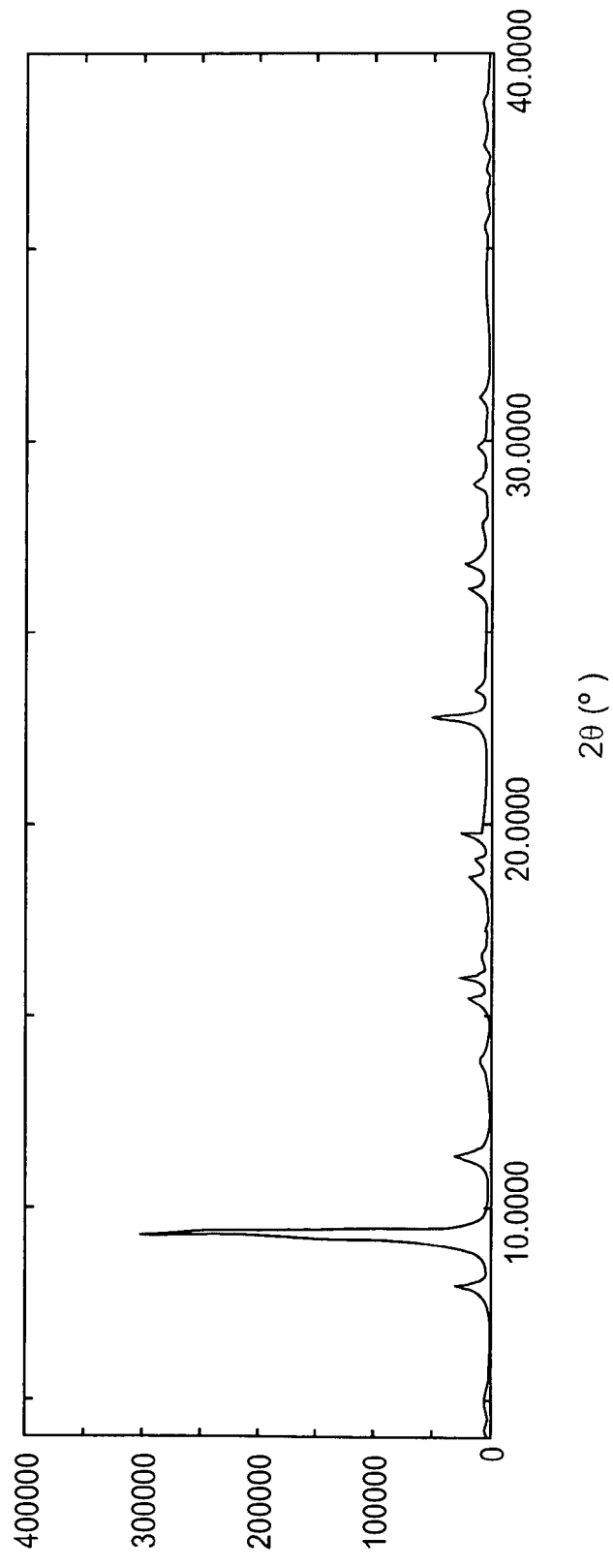
FIG. 4 shows an X-ray powder diffraction pattern of a crystal of compound 13b (monohydrate form of compound 13).
Figure 5:
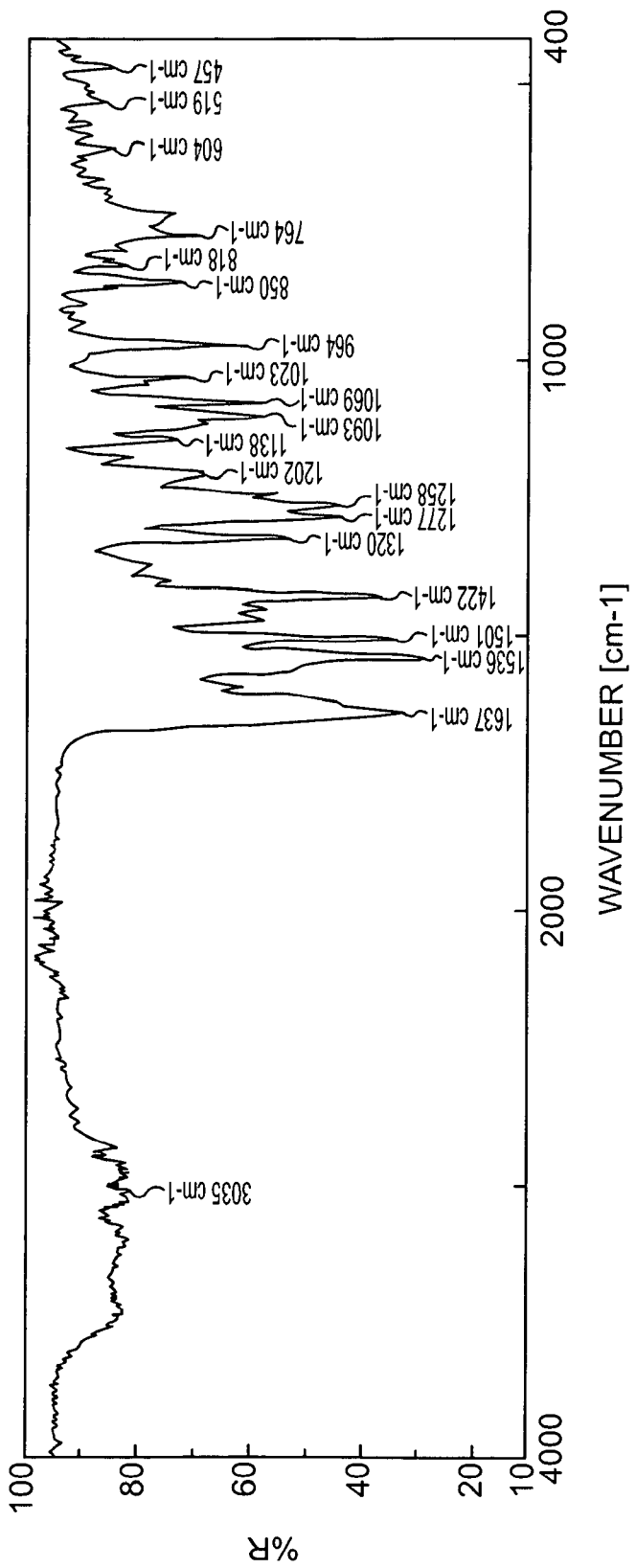
FIG. 5 shows an infrared absorption spectra of a crystal of compound 13b (monohydrate form of compound 13).

(14) A crystal form of (2) having one or more spectra selected from the group consisting of (d) and (e):
(d) X-ray powder diffraction pattern substantially as shown in FIG. 4; and
(e) Infrared absorption spectra substantially as shown in FIG. 5.

(15) A pharmaceutical composition containing the crystal form as defined in any one of (2) to (14).

(16) A process for preparation of the crystal forms as defined in any one of (2) to (14).

The present invention features crystalline forms of a salt of compound of formula AA, in particular a sodium salt.

The present invention features crystalline forms of a hydrate of a salt of a compound of formula AA, in particular a sodium salt.

This invention also includes a crystal form of a compound of formula AA (Compound 12, Example 1). Details are shown as (17) to (22):

(17) A crystal form of a compound of formula AA:

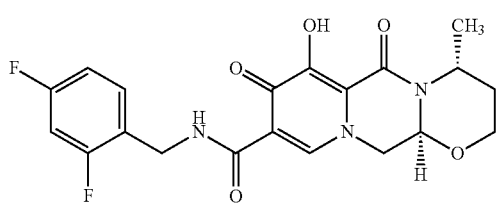

having one or more physical properties selected from the group consisting of (v) and (vi):

(v) having characteristic diffraction peaks at 5.4°±0.2°, 10.7°±0.2°, 12.3°±0.2°, 15.2°±0.2°, and 16.4°±0.2° degrees two-theta in an X-ray powder diffraction pattern; and (vi) having characteristic infrared absorption spectra at 1658 cm$^{-1}$±2 cm$^{-1}$, 1628 cm$^{-1}$±2 cm$^{-1}$, 1540 cm$^{-1}$±2 cm$^{-1}$ and 1498 cm$^{-1}$±2 cm$^{-1}$.

(18) A crystal form of a compound of formula AA:

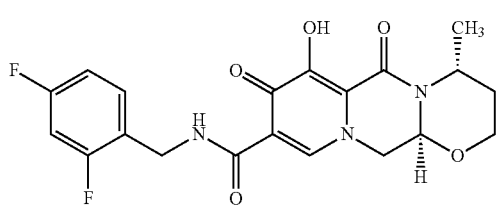

having characteristic diffraction peaks at 5.4°±0.2°, 10.7°±0.2°, 12.3°±0.2°, 15.2°±0.2° and 16.4°±0.2° degrees two-theta in an X-ray powder diffraction pattern.

(19) A crystal form of a compound of formula AA:

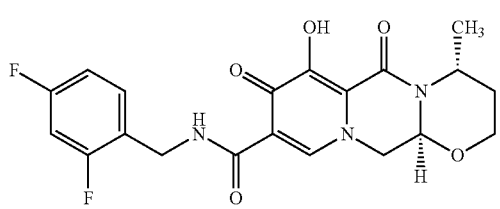

having characteristic diffraction peaks at 5.4°±0.2°, 10.7°±0.2°, 12.3°±0.2°, 14.3°±0.2°, 15.2°±0.2°, 16.4°±0.2°, 21.7°±0.2°, 24.9°±0.2°, 25.4°±0.2° and 27.9°±0.2° degrees two-theta in an X-ray powder diffraction pattern.

(20) A crystal of a compound of formula AA:

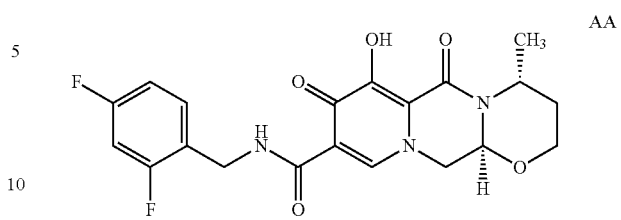

having characteristic infrared absorption spectra at 1658 cm$^{-1}$±2 cm$^{-1}$, 1628 cm$^{-1}$±2 cm$^{-1}$, 1540 cm$^{-1}$±2 cm$^{-1}$ and 1498 cm$^{-1}$±2 cm$^{-1}$.

(21) A crystal of a compound of formula AA:

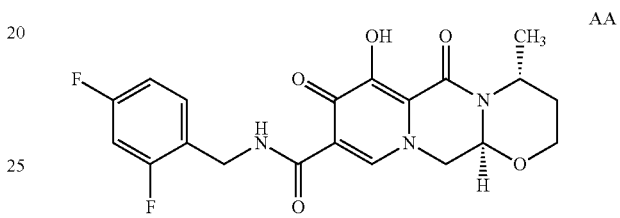

having characteristic infrared absorption spectra at 1658 cm$^{-1}$±2 cm$^{-1}$, 1628 cm$^{-1}$±2 cm$^{-1}$, 1540 cm$^{-1}$±2 cm$^{-1}$, 1498 cm$^{-1}$±2 cm$^{-1}$, 1355 cm$^{-1}$±2 cm$^{-1}$, 1264 cm$^{-1}$±2 cm$^{-1}$, 1238 cm$^{-1}$±2 cm$^{-1}$, 1080 cm$^{-1}$±2 cm$^{-1}$ and 1056 cm$^{-1}$±2 cm$^{-1}$.

Figure 6:
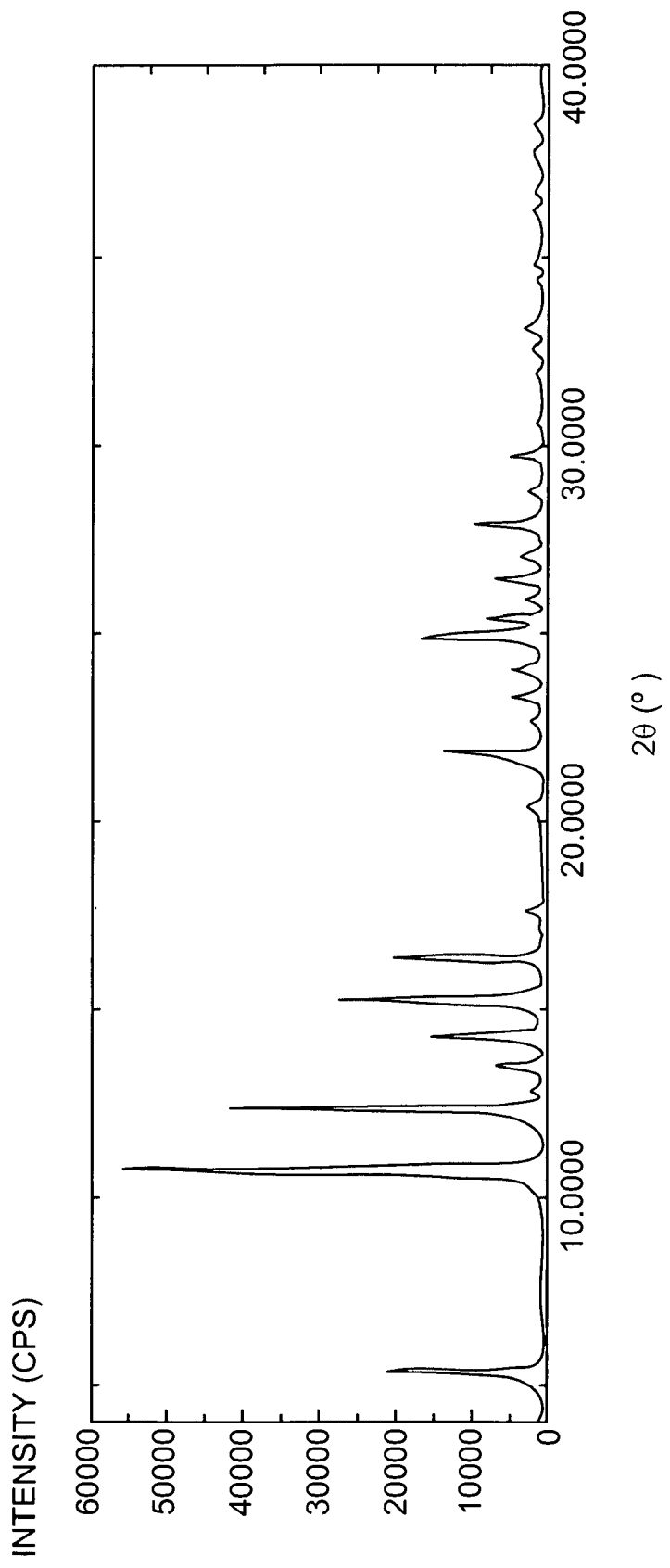
FIG. 6 shows an X-ray powder diffraction pattern of a crystal of compound 12.
Figure 7:
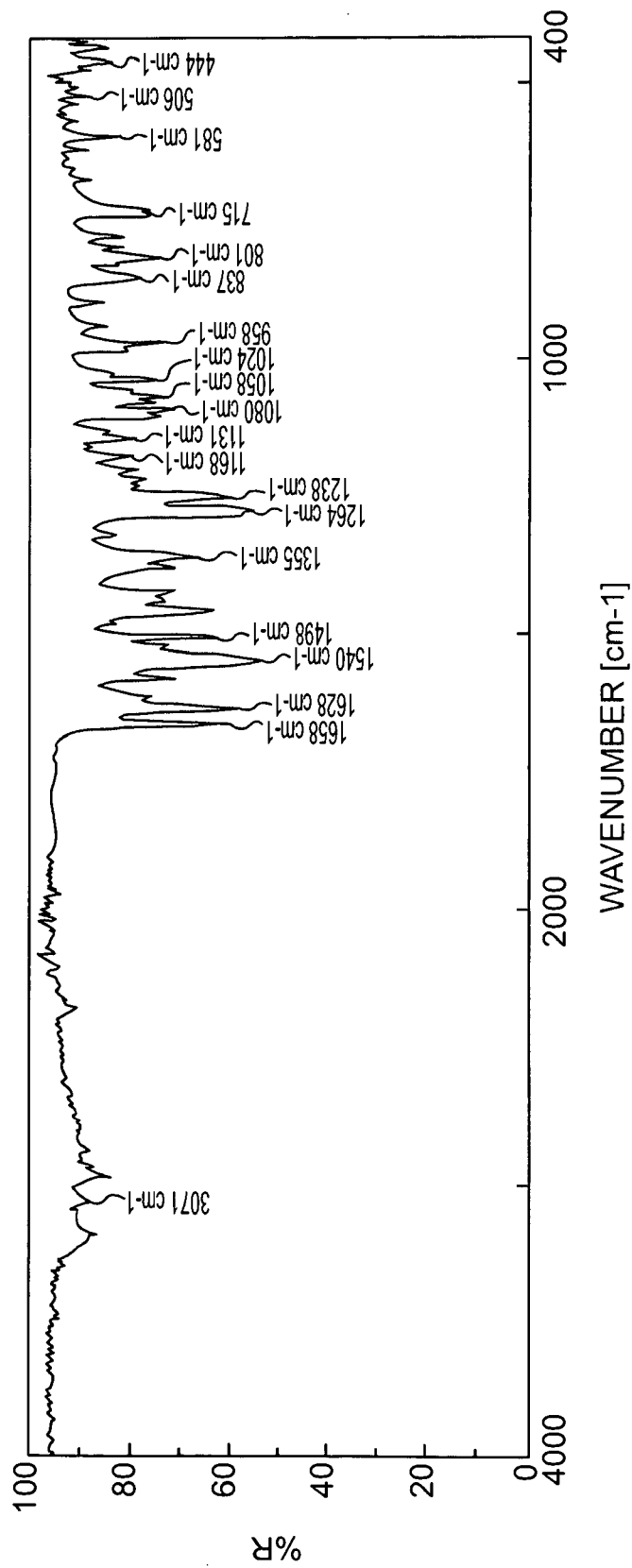
FIG. 7 shows an infrared absorption spectra of a crystal of compound 12.

(22) A crystal of a compound of formula AA:

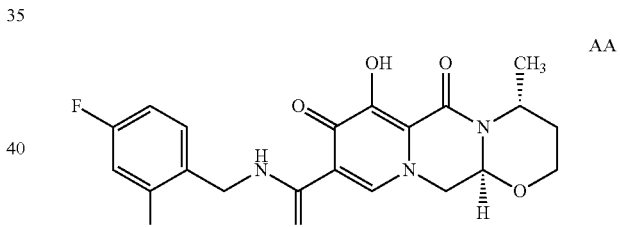

having one or, more spectra selected from the group consisting of (f) and (g):

(f) X-ray powder diffraction pattern substantially as shown in FIG. 6; and (g) Infrared absorption spectra substantially as shown in FIG. 7.

The crystals of compound 13 and 13b (monohydrate form of compound 13) demonstrate high solubility in water or saline, high bioavailability (BA), high maximum drug concentration (Cmax), short maximum drug concentration time (Tmax), high stability against heat or light, and/or good handling facility. Therefore, the crystals of compound 13 and 13b are suitable as pharmaceutical ingredients.

In the following examples and throughout this specification, the following abbreviations may be used: Me (methyl), Bn (benzyl), Aq (aqueous), Et (ethyl), C (centigrade).

EXAMPLES

In the following Examples, those depicting the bromination and amidation reactions of the present invention include Examples C, Example 2 and Example CC.

The following examples are intended for illustration only and are not intended to limit the scope of the invention in any way.

Examples 1 and 3

The starting material of Example 1e and 3e is the compound of formula (IIa) which is also shown as compound 5 below and compound #101 at page 113 of WO 2006/116764. The product depicted below as compound 8 is of the formula (I). The final product shown below as compound 13 is a compound of formula (I-7) at page 240 of WO 2006/116764 wherein $(R)_m$ is 2,4-di-F and $R^a$ is H, provided, however, that there is an alpha methyl at the position designated $R^{16}$ in formula (XXVI) at page 65.

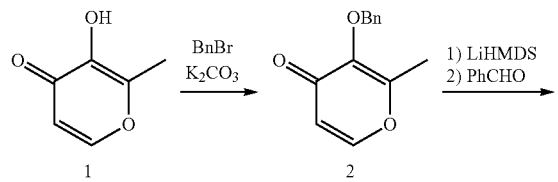

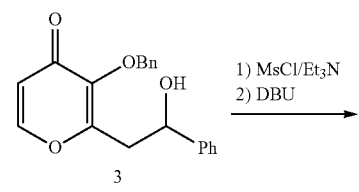

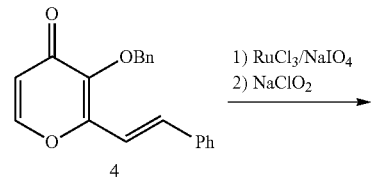

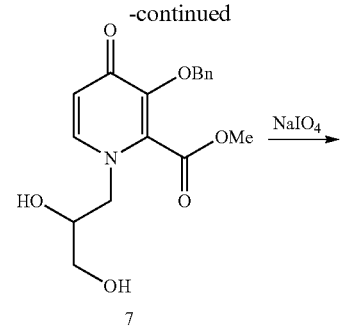

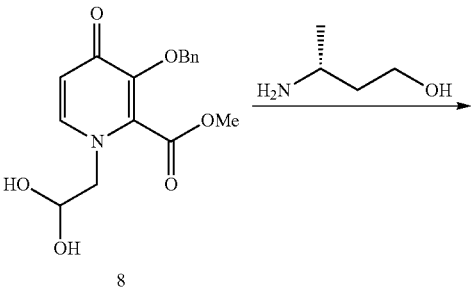

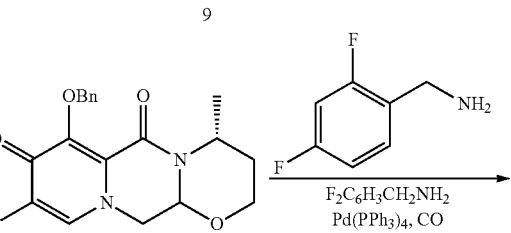

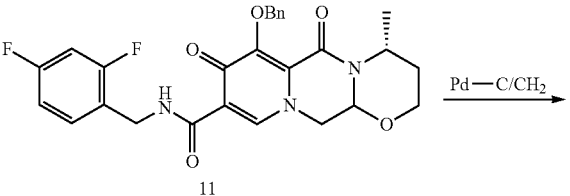

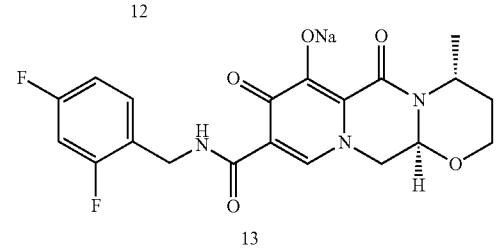

Thus, in the above sequence for Example 1, compound 5 is identical to compound 101 at page 113 of WO 2006/116764 and to formula (IIa) of the process of the present invention; compound 6 above is identical to formula (VIa) of the process of the present invention; compound 7 above is identical to formula (VIb) of the process of the present invention; and compound 8 is identical to formula (Ia) of the process of the present invention. Step i) of the invention process is 5 to 6 above while step ii) is 6 to 8.

Example 1a

To a slurry of 2000 g of compound 1(1.0 eq.) in 14.0 L of MeCN were added 2848 g of benzyl bromide (1.05 eq.) and 2630 g of $K_2CO_3$(1.2 eq.). The mixture was stirred at 80° C. for 5 h and cooled to 13° C. Precipitate was filtered and washed with 5.0 L of MeCN. The filtrate was concentrated and 3.0 L of THF was added to the residue. The THF solution was concentrated to give 3585 g of crude compound 2 as oil. Without further purification, compound 2 was used in the next step.
$^1$H NMR (300 MHz, $CDCl_3$) δ 7.60 (d, J=5.7 Hz, 1H), 7.4-7.3 (m, 5H), 6.37 (d, J=5.7 Hz, 1H), 5.17 (s, 2H), 2.09 (s, 3H).

Example 1b

To 904 g of the crude compound 2 was added 5.88 L of THF and the solution was cooled to −60° C. 5.00 L of 1.0M of Lithium bis(trimethylsilylamide) in THF (1.25 eq.) was added dropwise for 2 h to the solution of compound 2 at −60° C. Then, a solution of 509 g of benzaldehyde (1.2 eq.) in 800 mL of THF was added at −60° C. and the reaction mixture was aged at −60° C. for 1 h. The THF solution was poured into a mixture of 1.21 L of conc.HCl, 8.14 L of ice water and 4.52 L of EtOAc at less than 2° C. The organic layer was washed with 2.71 L of brine (twice) and the aqueous layer was extracted with 3.98 L of EtOAc. The combined organic layers were concentrated. To the mixture, 1.63 L of toluene was added and concentrated (twice) to provide toluene slurry of compound 3. Filtration, washing with 0.90 L of cold toluene and drying afforded 955 g of compound 3 (74% yield from compound 1) as a crystal.
$^1$H NMR (300 MHz, $CDCl_3$) δ 7.62 (d, J=5.7 Hz, 1H), 7.5-7.2 (m, 10H), 6.38 (d, J=5.7 Hz, 1H), 5.16 (d, J=11.4 Hz, 1H), 5.09 (d, J=11.4 Hz, 1H), 4.95 (dd, J=4.8, 9.0 Hz, 1H), 3.01 (dd, J=9.0, 14.1 Hz, 1H), 2.84 (dd, J=4.8, 14.1 Hz, 1H).

Example 1c

To a solution of 882 g of compound 3 (1.0 eq.) in 8.82 L of THF were added 416 g of $Et_3N$ (1.5 eq.) and 408 g of methanesulfonyl chloride (1.3 eq.) at less than 30° C. After confirmation of disappearance of compound 3, 440 mL of NMP and 1167 g of DBU (2.8 eq.) were added to the reaction mixture at less than 30° C. and the reaction mixture was aged for 30 min. The mixture was neutralized with 1.76 L of 16% sulfuric acid and the organic layer was washed with 1.76 L of 2% $Na_2SO_3$ aq. After concentration of the organic layer, 4.41 L of toluene was added and the mixture was concentrated (tree times). After addition of 4.67 L of hexane, the mixture was cooled with ice bath. Filtration, washing with 1.77 L of hexane and drying provided 780 g of compound 4 (94% yield) as a crystal.
$^1$H NMR (300 MHz, $CDCl_3$) δ 7.69 (d, J=5.7 Hz, 1H), 7.50-7.25 (m, 10H), 7.22 (d, J=16.2 Hz, 1H), 7.03 (d, J=16.2 Hz, 1H), 6.41 (d, J=5.7 Hz, 1H), 5.27 (s, 2H).

Example 1d

To a mixture of 822 g of compound 4 (1.0 eq.) and 11.2 g of $RuCl_3.nH_2O$ (0.02 eq.) in 2.47 L of MeCN, 2.47 L of EtOAc and 2.47 L of $H_2O$ was added 2310 g of $NaIO_4$(4.0 eq.) at less than 25° C. After aging for 1 h, 733 g of $NaClO_2$(3.0 eq.) was added to the mixture at less than 25° C. After aging for 1 h, precipitate was filtered and washed with 8.22 L of EtOAc. To the filtrate, 1.64 L of 50% $Na_2S_2O_3$ aq, 822 mL of $H_2O$ and 630 mL of conc.HCl were added. The aqueous layer was extracted with 4.11 L of EtOAc and the organic layers were combined and concentrated. To the residue, 4 L of toluene was added and the mixture was concentrated and cooled with ice bath. Filtration, washing with 1 L of toluene and drying provided 372 g of compound 5 (56% yield) as a crystal.
$^1$H NMR (300 MHz, $CDCl_3$) δ 7.78 (d, J=5.7 Hz, 1H), 7.54-7.46 (m, 2H), 7.40-7.26 (m, 3H), 6.48 (d, J=5.7 Hz, 1H), 5.6 (brs, 1H), 5.31 (s, 2H).

Example 1e

A mixture of 509 g of compound 5 (1.0 eq.) and 407 g of 3-amino-propane-1,2-diol (2.5 eq.) in 1.53 L of EtOH was stirred at 65° C. for 1 h and at 80° C. for 6 h. After addition of 18.8 g of 3-Amino-propane-1,2-diol (0.1 eq.) in 200 mL of EtOH, the mixture was stirred at 80° C. for 1 h. After addition of 18.8 g of 3-amino-propane-1,2-diol (0.1 eq.) in 200 mL of EtOH, the mixture was stirred at 80° C. for 30 min. After cooling and addition of 509 mL of $H_2O$, the mixture was concentrated. To the residue, 2.54 L of $H_2O$ and 2.54 L of AcOEt were added. After separation, the aqueous layer was washed with 1.02 L of EtOAc. To the aqueous layer, 2.03 L of 12% sulfuric acid was added at less than 12° C. to give crystal of compound 6. Filtration, washing with 1.53 L of cold $H_2O$ and drying provided 576 g of compound 6 (83% yield) as a crystal.
$^1$H NMR (300 MHz, DMSO-$d_6$) δ 7.67 (d, J=7.5 Hz, 1H), 7.5-7.2 (m, 5H), 6.40 (d, J=7.5 Hz, 1H), 5.07 (s, 2H), 4.2-4.0 (m, 1H), 3.9-3.6 (m, 2H), 3.38 (dd, J=4.2, 10.8 Hz, 1H), 3.27 (dd, J=6.0, 10.8 Hz, 1H).

Example 1f

To a slurry of 576 g of compound 6(1.0 eq.: 5.8% of $H_2O$ was contained) in 2.88 L of NMP were added 431 g of $NaHCO_3$(3.0 eq.) and 160 mL of methyl iodide (1.5 eq.) and the mixture was stirred at room temperature for 4 h. After cooling to 5° C., 1.71 L of 2N HCl and 1.15 L of 20% NaClaq were added to the mixture at less than 10° C. to give crystal of compound 7. Filtration, washing with 1.73 L of $H_2O$ and drying provided 507 g of compound 7 (89% yield) as a crystal.
$^1$H NMR (300 MHz, DMSO-$d_6$) δ 7.59 (d, J=7.5 Hz, 1H), 7.40-7.28 (m, 5H), 6.28 (d, J=7.5 Hz, 1H), 5.21 (d, J=5.4 Hz, 1H), 5.12 (d, J=10.8 Hz, 1H), 5.07 (d, J=10.8 Hz, 1H), 4.83 (t, J=5.7 Hz, 1H), 3.97 (dd, J=2.4, 14.1 Hz, 1H), 3.79 (s, 3H), 3.70 (dd, J=9.0, 14.4 Hz, 1H), 3.65-3.50 (m, 1H), 3.40-3.28 (m, 1H), 3.26-3.14 (m, 1H).

Example 1 g

To a mixture of 507 g of compound 7(1.0 eq.) in 5.07 L of MeCN, 5.07 L of $H_2O$ and 9.13 g of AcOH (0.1 eq.) was added 390 g of $NaIO_4$(1.2 eq.) and the mixture was stirred at room temperature for 2 h. After addition of 1.52 L of 10% $Na_2S_2O_3$ aq., the mixture was concentrated and cooled to 10°

C. Filtration, washing with H$_2$O and drying provided 386 g of compound 8 (80% yield) as a crystal.

$^1$H NMR (300 MHz, DMSO-d$_6$) δ 7.62 (d, J=7.5 Hz, 1H), 7.42-7.30 (m, 5H), 6.33 (d, J=6.0 Hz, 2H), 6.29 (d, J=7.5 Hz, 1H), 5.08 (s, 2H), 4.95-4.85 (m, 1H), 3.80 (s, 3H), 3.74 (d, J=5.1 Hz, 2H).

Example 1h

After dissolution of a mixture of 378 g of compound 8 (1.0 eq.) in 3.78 L of MeOH by heating, the solution was concentrated. To the residue, 1.51 L of toluene was added and the mixture was concentrated. To the residue, 1.89 L of toluene, 378 mL of AcOH and 137 g of (R)-3-Amino-butan-1-ol (1.3 eq.) were added and the mixture was heated to 90° C., stirred at 90° C. for 2.5 h and concentrated. To the residue, 1.89 L of toluene was added and the mixture was concentrated. The residue was extracted with 3.78 L and 1.89 L of CHCl$_3$ and washed with 2×1.89 L of H$_2$O. The organic layers were combined and concentrated. To the residue, 1.89 L of EtOAc was added and the mixture was concentrated. After addition of 1.89 L of EtOAc, filtration, washing with 1.13 L of EtOAc and drying provided 335 g of compound 9 (83% yield) as a crystal.

$^1$H NMR (300 MHz, CDCl$_3$) δ 7.70-7.58 (m, 2H), 7.40-7.24 (m, 3H), 7.14 (d, J=7.5 Hz, 2H), 6.47 (d, J=7.5 Hz, 1H), 5.35 (d, J=10.2 Hz, 1H), 5.28 (d, J=10.2 Hz, 1H), 5.12 (dd, J=3.9, 6.3 Hz, 1H), 5.05-4.90 (m, 1H), 4.07 (dd, J=3.9, 13.5 Hz, 1H), 4.00-3.86 (m, 3H), 2.23-2.06 (m, 1H), 1.48 (ddd, J=2.4, 4.5, 13.8 Hz, 1H), 1.30 (d, J=6.9 Hz, 3H).

Example 1i

To a slurry of 332 g of compound 9 (1.0 eq.) in 1.66 L of NMP was added 191 g of NBS (1.1 eq.) and the mixture was stirred at room temperature for 2 h. After addition of 1.26 L of H$_2$O, the mixture was stirred for 30 min. After addition of 5.38 L of H$_2$O and aging of the mixture at 10° C. for 30 min and at 5° C. for 1 h, filtration, washing with 1.33 L of cold H$_2$O and drying provided 362 g of compound 10 (89% yield) as a crystal.

$^1$H NMR (300 MHz, CDCl$_3$) δ 7.69-7.63 (m, 2H), 7.59 (s, 1H), 7.38-7.24 (m, 3H), 5.33 (d, J=10.2 Hz, 1H), 5.25 (d, J=9.9 Hz, 1H), 5.12 (dd, J=3.9, 5.7 Hz, 1H), 5.05-4.90 (m, 1H), 4.11 (dd, J=3.9, 13.2 Hz, 1H), 4.02-3.88 (m, 3H), 2.21-2.06 (m, 1H), 1.49 (ddd, J=2.4, 4.5, 14.1 Hz, 1H), 1.31 (d, J=6.9 Hz, 3H).

Example 1j

Under carbon mono-oxide atmosphere, a mixture of 33.5 g of compound 10 (1.0 eq.), 34.8 mL of i-Pr$_2$NEt (2.5 eq.), 14.3 mL of 2,4-difluorobenzylamine (1.5 eq.) and 4.62 g of Pd(PPh$_3$)$_4$ (0.05 eq.) in 335 mL of DMSO was stirred at 90° C. for 5.5 h. After cooling, precipitate was filtered and washed with 50 mL of 2-propanol. After addition of 502 mL of H$_2$O and 670 mL of AcOEt to the filtrate, the organic layer was washed with 335 mL of 0.5N HClaq. and 335 mL of H$_2$O and the aqueous layer was extracted with 335 mL of AcOEt. The organic layers were combined and concentrated. To the residue, 150 mL of 2-propanol was added and the mixture was concentrated. After addition of 150 mL of 2-propanol, concentration, cooling to 20° C. and filtration, crude crystal of compound 11 was obtained. After dissolution of the crude crystal in 380 mL of acetone by heating, precipitate was filtered and the filtrate was concentrated. After addition of 200 mL of EtOH, concentration, addition of 150 mL of EtOH, concentration, cooling and filtration, crude crystal of compound 11 was obtained. After dissolution of the crude crystal in 450 mL of acetone by heating, the solution was concentrated. To the residue, 150 mL of 2-propanol was added and the mixture was concentrated (twice). After cooling of the residue, filtration, washing with 2-propanol and drying provided 34.3 g of compound 11 (84% yield) as a crystal.

$^1$H NMR (300 MHz, CDCl$_3$) δ 10.40 (t, J=6.0 Hz, 1H), 8.35 (s, 1H), 7.66-7.58 (m, 2H), 7.42-7.24 (m, 5H), 6.78-6.74 (m, 2H), 5.30 (d, J=9.9 Hz, 1H), 5.26 (d, J=10.2 Hz, 1H), 5.15 (dd, J=3.9, 5.7 Hz, 1H), 5.05-4.90 (m, 1H), 4.64 (d, J=5.4 Hz, 2H), 4.22 (dd, J=3.9, 13.5, 1H), 4.09 (dd, J=6.0, 13.2 Hz, 1H), 4.02-3.88 (m, 2H), 2.24-1.86 (m, 1H), 1.50 (ddd, J=2.4, 4.5, 14.1 Hz, 1H), 1.33 (d, J=7.2 Hz, 3H).

Example 1k

Under hydrogen atmosphere, a mixture of 28.0 g of compound 11 (1.0 eq.) and 5.6 g of 10% Pd—C in 252 mL of THF and 28 mL of MeOH was stirred for 1 h. After precipitate (Pd—C) was filtered and washed with 45 mL of THF, 5.6 g of 10% Pd—C was added and the mixture was stirred for 1.5 h under hydrogen atmosphere. After Pd—C was filtered and washed with 150 mL of CHCl$_3$/MeOH (9/1), the filtrate was concentrated. After dissolution of the residue in 1.38 L of EtOH by heating, the solution was gradually cooled to room temperature. After filtration, the filtrate was concentrated and cooled. Filtration, washing with EtOH and drying provided 21.2 g of compound 12 (92% yield) as a crystal.

$^1$H NMR (300 MHz, DMSO-d$_6$) δ 12.51 (s, 1H), 10.36 (t, J=5.7 Hz, 1H), 8.50 (s, 1H), 7.39 (td, J=8.7, 6.3 Hz, 1H), 7.24 (ddd, J=2.6, 9.5, 10.8 Hz, 1H), 7.12-7.00 (m, 1H), 5.44 (dd, J=3.9, 5.7 Hz, 1H), 4.90-4.70 (m, 1H), 4.65-4.50 (m, 1H), 4.54 (d, J=5.1 Hz, 2H), 4.35 (dd, J=6.0, 13.8 Hz, 1H), 4.10-3.98 (m, 1H), 3.96-3.86 (m, 1H), 2.10-1.94 (m, 1H), 1.60-1.48 (m, 1H), 1.33 (d, J=6.9 Hz, 3H).

Example 1l

After dissolution of 18.0 g of compound 12 (1.0 eq.) in 54 mL of EtOH by heating, followed by filtration, 21.5 mL of 2N NaOHaq. (1.0 eq.) was added to the solution at 80° C. The solution was gradually cooled to room temperature. Filtration, washing with 80 mL of EtOH and drying provided. 18.8 g of compound 13 (99% yield) as a crystal.

$^1$H NMR (300 MHz, DMSO-d$_6$) δ 10.70 (t, J=6.0 Hz, 1H), 7.89 (s, 1H), 7.40-7.30 (m, 1H), 7.25-7.16 (m, 1H), 7.06-6.98 (m, 1H), 5.22-5.12 (m, 1H), 4.87-4.74 (m, 1H), 4.51 (d, J=5.4 Hz, 2H), 4.35-4.25 (m, 1H), 4.16 (dd, J=1.8, 14.1 Hz, 1H), 4.05-3.90 (m, 1H), 3.86-3.74 (m, 1H), 2.00-1.72 (m, 1H), 1.44-1.32 (m, 1H), 1.24 (d, J=6.9 Hz, 3H).

Example 1m

Example 1m shows a process for preparation of the crystalline compound 13b which is monohydrate form of compound 13.

After dissolution of 30.0 g of compound 13 (1.0 eq.) in 600 mL of THF-water solution (8:2) by 30° C., 36.0 mL of 2N NaOHaq (1.0 eq.) was added to the solution. The mixture was stirred at room temperature for 2 hours. The precipitation was filtered, washing with 150 mL of TI-IF-water solution (8:2), 150 mL of THF. Drying at 85° C. and humidity conditioning provided 30.4 g of compound 13b (monohydrate form of compound 13, 93% yield) as a crystal.

Example 3

Example 3a

To a slurry of 2000 g of compound 1 (1.0 eq.) in 14.0 L of MeCN were added 2848 g of benzyl bromide (1.05 eq.) and 2630 g of $K_2CO_3$ (1.2 eq.). The mixture was stirred at 80° C. for 5 h and cooled to 13° C. Precipitate was filtered and washed with 5.0 L of MeCN. The filtrate was concentrated and 3.0 L of THF was added to the residue. The THF solution was concentrated to give 3585 g of crude compound 2 as oil. Without further purification, compound 2 was used in the next step.

$^1$H NMR (300 MHz, $CDCl_3$) δ 7.60 (d, J=5.7 Hz, 1H), 7.4-7.3 (m, 5H), 6.37 (d, J=5.7 Hz, 1H), 5.17 (s, 2H), 2.09 (s, 3H).

Example 3b

To 904 g of the crude compound 2 was added 5.88 L of THF and the solution was cooled to −60° C. 5.00 L of 1.0M of Lithium bis(trimethylsilyl)amide in THF (1.25 eq.) was added dropwise for 2 h to the solution of compound 2 at −60° C. Then, a solution of 509 g of benzaldehyde (1.2 eq.) in 800 mL of THF was added at −60° C. and the reaction mixture was aged at −60° C. for 1 h. The THF solution was poured into a mixture of 1.21 L of conc.HCl, 8.14 L of ice water and 4.52 L of EtOAc at less than 2° C. The organic layer was washed with 2.71 L of brine (twice) and the aqueous layer was extracted with 3.98 L of EtOAc. The combined organic layers were concentrated. To the mixture, 1.63 L of toluene was added and concentrated (twice) to provide toluene slurry of compound 3. Filtration, washing with 0.90 L of cold toluene and drying afforded 955 g of compound 3 (74% yield from compound 1) as a crystal.

$^1$H NMR (300 MHz, $CDCl_3$) δ 7.62 (d, J=5.7 Hz, 1H), 7.5-7.2 (m, 10H), 6.38 (d, J=5.7 Hz, 1H), 5.16 (d, J=11.4 Hz, 1H), 5.09 (d, J=11.4 Hz, 1H), 4.95 (dd, J=4.8, 9.0 Hz, 1H), 3.01 (dd, J=9.0, 14.1 Hz, 1H), 2.84 (dd, J=4.8, 14.1 Hz, 1H).

Example 3c

To a solution of 882 g of compound 3 (1.0 eq.) in 8.82 L of THF were added 416 g of $Et_3N$ (1.5 eq.) and 408 g of methanesulfonyl chloride (1.3 eq.) at less than 30° C. After confirmation of disappearance of compound 3, 440 mL of NMP and 1167 g of DBU (2.8 eq.) were added to the reaction mixture at less than 30° C. and the reaction mixture was aged for 30 min. The mixture was neutralized with 1.76 L of 16% sulfuric acid and the organic layer was washed with 1.76 L of 2% $Na_2SO_3$ aq. After concentration of the organic layer, 4.41 L of toluene was added and the mixture was concentrated (tree times). After addition of 4.67 L of hexane, the mixture was cooled with ice bath. Filtration, washing with 1.77 L of hexane and drying provided 780 g of compound 4 (94% yield) as a crystal.

$^1$H NMR (300 MHz, $CDCl_3$) δ 7.69 (d, J=5.7 Hz, 1H), 7.50-7.25 (m, 10H), 7.22 (d, J=16.2 Hz, 1H), 7.03 (d, J=16.2 Hz, 1H), 6.41 (d, J=5.7 Hz, 1H), 5.27 (s, 2H).

Example 3d

To a mixture of 10.0 g of compound 4 and 13.6 mg of $RuCl_3 \cdot nH_2O$ in 95 mL of MeCN and 10 mL of water, mixture of 155 mL of water, 7.2 g of hydrosulfuric acid, and 15.5 g of $NaIO_4$ was added for 2.5 h at 20° C. After aging for 1 h, organic and aqueous layers were separated and aqueous layer was extracted by 30 mL of ethyl acetate. Aqueous layer was extracted again by 30 mL of ethyl acetate and organic layers were combined. 6 mL of 5% NaHSO3 solution was added to the combined organic layer and the layers were separated. The organic layer was adjusted to pH 6.0 by adding 4.0 g of 2M NaOH solution and the aqueous layer was separated. After 60 mL of 5% $NaHCO_3$ solution and 257 mg of TEMPO was added, 25.9 g of NaClO solution was added to the reaction mixture at 25° C. for 1 h and stirred for 30 min to check the reaction was finished. After the layers were separated, 42.5 mL of 5% Na2SO3 solution and 30 mL of AcOEt were added and separated. The aqueous layer was extracted by 30 mL of AcOEt and separated. 12% $H_2SO_4$ was added to the reaction mixture at 20° C. for 1 h and the mixture was cooled to 5° C. After the mixture was stirred for 30 min, the mixture was filtered, washed with 30 mL of water twice and dried to provide 5.7 g of compound 5 (70% yield) as a crystal.

$^1$H NMR (300 MHz, $CDCl_3$) δ 7.78 (d, J=5.7 Hz, 1H), 7.54-7.46 (m, 2H), 7.40-7.26 (m, 3H), 6.48 (d, J=5.7 Hz, 1H), 5.6 (brs, 1H), 5.31 (s, 2H).

Example 3e

A mixture of 509 g of compound 5 (1.0 eq.) and 407 g of 3-amino-propane-1,2-diol (2.5 eq.) in 1.53 L of EtOH was stirred at 65° C. for 1 h and at 80° C. for 6 h. After addition of 18.8 g of 3-Amino-propane-1,2-diol (0.1 eq.) in 200 mL of EtOH, the mixture was stirred at 80° C. for 1 h. After addition of 18.8 g of 3-amino-propane-1,2-diol (0.1 eq.) in 200 mL of EtOH, the mixture was stirred at 80° C. for 30 min. After cooling and addition of 509 mL of $H_2O$, the mixture was concentrated. To the residue, 2.54 L of $H_2O$ and 2.54 L of AcOEt were added. After separation, the aqueous layer was washed with 1.02 L of EtOAc. To the aqueous layer, 2.03 L of 12% sulfuric acid was added at less than 12° C. to give crystal of compound 6. Filtration, washing with 1.53 L of cold $H_2O$ and drying provided 576 g of compound 6 (83% yield) as a crystal.

$^1$H NMR (300 MHz, DMSO-$d_6$) δ 7.67 (d, J=7.5 Hz, 1H), 7.5-7.2 (m, 5H), 6.40 (d, J 7.5 Hz, 1H), 5.07 (s, 2H), 4.2-4.0 (m, 1H), 3.9-3.6 (m, 2H), 3.38 (dd, J=4.2, 10.8 Hz, 1H), 3.27 (dd, J=6.0, 10.8 Hz, 1H).

Example 3f

To a slurry of 576 g of compound 6 (1.0 eq.: 5.8% of $H_2O$ was contained) in 2.88 L of NMP were added 431 g of $NaHCO_3$ (3.0 eq.) and 160 mL of methyl iodide (1.5 eq.) and the mixture was stirred at room temperature for 4 h. After cooling to 5° C., 1.71 L of 2N HCl and 1.15 L of 20% NaClaq were added to the mixture at less than 10° C. to give crystal of compound 7. Filtration, washing with 1.73 L of $H_2O$ and drying provided 507 g of compound 7 (89% yield) as a crystal.

$^1$H NMR (300 MHz, DMSO-$d_6$) δ 7.59 (d, J=7.5 Hz, 1H), 7.40-7.28 (m, 5H), 6.28 (d, J=7.5 Hz, 1H), 5.21 (d, J=5.4 Hz, 1H), 5.12 (d, J=10.8 Hz, 1H), 5.07 (d, J=10.8 Hz, 1H), 4.83 (t, J=5.7 Hz, 1H), 3.97 (dd, J=2.4, 14.1 Hz, 1H), 3.79 (s, 3H), 3.70 (dd, J=9.0, 14.4 Hz, 1H), 3.65-3.50 (m, 1H), 3.40-3.28 (m, 1H), 3.26-3.14 (m, 1H).

Example 3 g

To a mixture of 15.0 g of compound 7 (1.0 eq.) in 70.9 g of MeCN, a mixture of 60 mL of $H_2O$, 2.6 g of $H_2SO_4$ and 11.5 g of $NaIO_4$ was added in the range between 17° C. to 14° C. After the reaction mixture was stirred for 1 hour, precipitate was filtered. The filtrate was added to the solution of 11.8 g of ascorbic acid sodium salt, 64 g of water and 60 mg of $H_2SO_4$. After the mixture was concentrated, cooling to 5° C., filtration, washing with $H_2O$ and drying provided 12.9 g of compound 8 (90% yield) as a crystal.

$^1$H NMR (300 MHz, DMSO-$d_6$) δ 7.62 (d, J=7.5 Hz, 1H), 7.42-7.30 (m, 5H), 6.33 (d, J=6.0 Hz, 2H), 6.29 (d, J=7.5 Hz, 1H), 5.08 (s, 2H), 4.95-4.85 (m, 1H), 3.80 (s, 3H), 3.74 (d, J=5.1 Hz, 2H).

Example 3 h

A mixture of 10.0 g of compound 8 and 33.3 g of diglyme were added the solution of 3.3 g of (R)-3-Amino-butan-1-ol in 4.7 g of diglyme and 1.0 g of acetic acid at 60° C. After the reaction mixture was stirred at 95° C. for 9 hours, the reaction mixture was cooled to −5° C. and filtered. The wet crystal was washed and dried to give 8.3 g of compound 9 (78%). XRD data:

$^1$H NMR (300 MHz, CDCl$_3$) δ 7.70-7.58 (m, 2H), 7.40-7.24 (m, 3H), 7.14 (d, J=7.5 Hz, 2H), 6.47 (d, J=7.5 Hz, 1H), 5.35 (d, J=10.2 Hz, 1H), 5.28 (d, J=10.2 Hz, 1H), 5.12 (dd, J=3.9, 6.3 Hz, 1H), 5.05-4.90 (m, 1H), 4.07 (dd, J=3.9, 13.5 Hz, 1H), 4.00-3.86 (m, 3H), 2.23-2.06 (m, 1H), 1.48 (ddd, J=2.4, 4.5, 13.8 Hz, 1H), 1.30 (d, J=6.9 Hz, 3H).

Example 3i

To slurry of 5.7 g of NBS in 26.5 g of dichloromethane was added 10 g of compound 9 in 92.8 g of dichloromethane at room temperature. After the reaction mixture was stirred for 6.5 h, the reaction mixture was added to the solution of 2.0 g Na2SO3 and 40.3 g of water. The organic layer was washed with diluted NaOH solution and water, dichloromethane was concentrated and was displaced by methanol. The mixture was cooled to −5° C. and filtered and the wet crystal was washed and dried to give 10.3 g of compound 10 (84%).

$^1$H NMR (300 MHz, CDCl$_3$) δ 7.69-7.63 (m, 2H), 7.59 (s, 1H), 7.38-7.24 (m, 3H), 5.33 (d, J=10.2 Hz, 1H), 5.25 (d, J=9.9 Hz, 1H), 5.12 (dd, J=3.9, 5.7 Hz, 1H), 5.05-4.90 (m, 1H), 4.11 (dd, J=3.9, 13.2 Hz, 1H), 4.02-3.88 (m, 3H), 2.21-2.06 (m, 1H), 1.49 (ddd, J=2.4, 4.5, 14.1 Hz, 1H), 1.31 (d, J=6.9 Hz, 3H).

Example 3j

Under carbon mono-oxide atmosphere, a mixture of 25.0 g of compound 10, 11.6 g of i-Pr$_2$NEt, 12.8 g of 2,4-difluorobenzylamine; 335 mg of Pd(OAc)$_2$ and 1.9 g of 1,4-bis(diphenylphosphino)butane in 188 mL of DMA was stirred at 85° C. for 4 h. After cooling, the reaction mixture was divided and $^{19}$⁄$_{25}$ of mixture was used for next step. 6.6 g of AcOEt, 29.9 g of water and 3 mg of seed crystal were added to the reaction mixture at 40° C. After stirring for 7 min, 29.9 g of water was added and cooled to room temperature. The crystal was filtered at room temperature and washed by 47.2 g of ethanol to give 10.1 g of compound 11 (83% yield) as a crystal.

$^1$H NMR (300 MHz, CDCl$_3$) δ 10.40 (t, J=6.0 Hz, 1H), 8.35 (s, 1H), 7.66-7.58 (m, 2H), 7.42-7.24 (m, 5H), 6.78-6.74 (m, 2H), 5.30 (d, J=9.9 Hz, 1H), 5.26 (d, J=10.2 Hz, 1H), 5.15 (dd, J=3.9, 5.7 Hz, 1H), 5.05-4.90 (m, 1H), 4.64 (d, J=5.4 Hz, 2H), 4.22 (dd, J=3.9, 13.5 Hz, 1H), 4.09 (dd, J=6.0, 13.2 Hz, 1H), 4.02-3.88 (m, 2H), 2.24-1.86 (m, 1H), 1.50 (ddd, J=2.4, 4.5, 14.1 Hz, 1H), 1.33 (d, J=7.2 Hz, 3H).

Example 3k

Under hydrogen atmosphere, a mixture of 4.0 g of compound 11 and 0.8 g of 50% wet 5% Pd—C in 67.6 mL of THF and 1.6 mL of $H_2O$ was stirred for 1.5 h at 50° C. After mixture of 80 mg of NaHSO$_3$ and 2.0 mL of purified water was added to the reaction mixture and the reaction mixture was stirred for 1 h, precipitate was filtered, washed with 20 mL of THF, and the filtrate was concentrated to 11.97 g. After adding 6.7 mL of ethanol and 33.6 mL of purified water over 1 h, reaction mixture was cooled to 25° C. Filtration, washing with 26.9 mL of EtOH and drying provided 2.33 g of compound 12 (82% yield) as a crystal.

$^1$H NMR (300 MHz, DMSO-$d_6$) δ 12.51 (s, 1H), 10.36 (t, J=5.7 Hz, 1H), 8.50 (s, 1H), 7.39 (td, J=8.7, 6.3 Hz, 1H), 7.24 (ddd, J=2.6, 9.5, 10.8 Hz, 1H), 7.12-7.00 (m, 1H), 5.44 (dd, J=3.9, 5.7 Hz, 1H), 4.90-4.70 (m, 1H), 4.65-4.50 (m, 1H), 4.54 (d, J=5.1 Hz, 2H), 4.35 (dd, J=6.0, 13.8 Hz, 1H), 4.10-3.98 (m, 1H), 3.96-3.86 (m, 1H), 2.10-1.94 (m, 1H), 1.60-1.48 (m, 1H), 1.33 (d, J=6.9 Hz, 3H).

Example 3l

After dissolution of 18.0 g of compound 12 (1.0 eq.) in 54 mL of EtOH by heating, followed by filtration, 21.5 mL of 2N NaOHaq. (1.0 eq.) was added to the solution at 80° C. The solution was gradually cooled to room temperature. Filtration, washing with 80 mL of EtOH and drying provided 18.8 g of compound 13 (99% yield) as a crystal.

$^1$H NMR (300 MHz, DMSO-$d_6$) δ 10.70 (t, J=6.0 Hz, 1H), 7.89 (s, 1H), 7.40-7.30 (m, 1H), 7.25-7.16 (m, 1H), 7.06-6.98 (m, 1H), 5.22-5.12 (m, 1H), 4.87-4.74 (m, 1H), 4.51 (d, J=5.4 Hz, 2H), 4.35-4.25 (m, 1H), 4.16 (dd, J=1.8, 14.1 Hz, 1H), 4.05-3.90 (m, 1H), 3.86-3.74 (m, 1H), 2.00-1.72 (m, 1H), 1.44-1.32 (m, 1H), 1.24 (d, J=6.9 Hz, 3H).

Apparatus and conditions used to generate FIGS. 1-7 are as follows:

Measurement of X-Ray Powder Diffraction Pattern

The measuring conditions used were the same as general metrology for the X-ray powder diffraction pattern measurement described in "The Japanese Pharmacopoeia Fifteenth Edition".

Measuring Apparatus
RINT TTR III
Methods
The acquisition conditions were as follows.
Measurement Method: parallel beam method
Tube anode: Cu
Radiation: Cu Kα
Generator current: 300 mA
Generator tension: 50 kV
The sample was prepared on an aluminum wafer
Angle of incidence: 4° and 40°
Measurement of Infrared Spectroscopy Analysis
The acquisition conditions used for were as follows.
Measuring Apparatus
FT/IR-4200typeA (by JASCO Corporation)
Methods
Measurement method: ATR (Attenuated total reflection) method
Resolution: 4 (cm-1)
Detector: DLATGS
Accumulation: 32 times
Measurement of Solid-State $^{13}$C NMR Spectra
The spectrum was obtained using the cross polarization magic-angle-spinning (CP/MAS) method. The acquisition conditions were as follows.
Measuring Apparatus
Spectrometer: Varian NMR Systems (1H frequency: 599.8 MHz)

Methods
Probe: 3.2 mm T3 HX Probe
Spectral width: 43103.4 Hz
Acquisition Time: 0.04 s
Recycle Delay: 10 s
Contact Time: 3 ms
External standard: adamantane (methyne carbon: 38.52 ppm)
Temperature: 10
MAS rate: 20 kHz Example A The starting material of Example A is compound 8, which is identical to formula (Ia). Thus, Example A depicts a process in providing an intermediate for the compound of formula 17 below which is isomeric to the compound ZZ-2 at page 237 of WO 2006/116764 to Brian Johns et al.

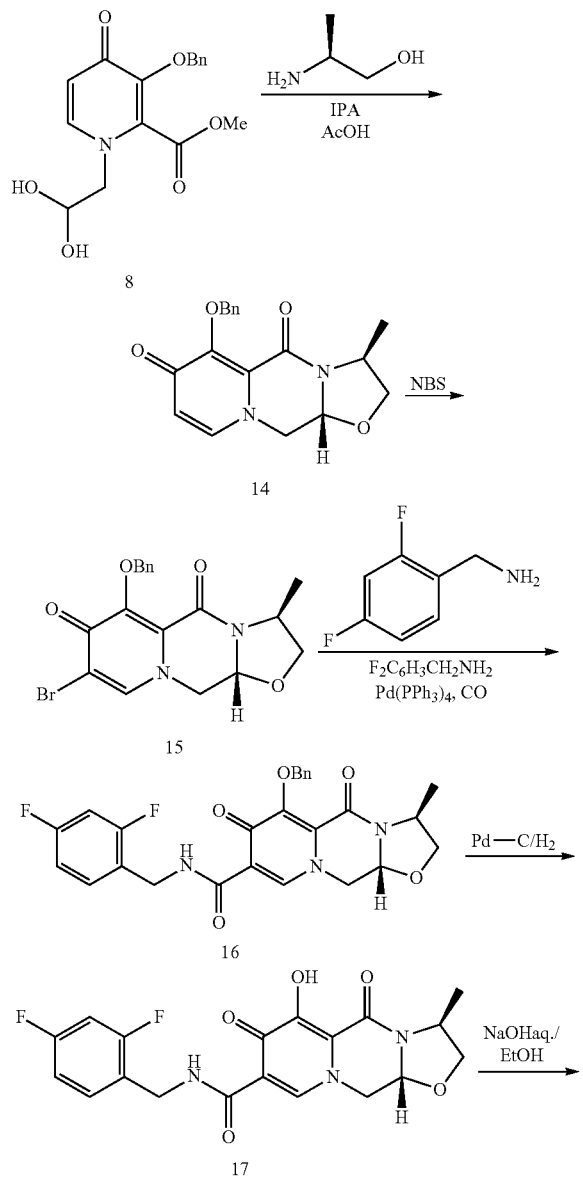

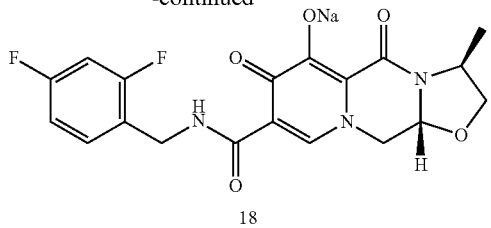

Example Aa

After dissolution of mixture of 320 g of compound 8 (1.0 eq.) in 3.20 L of MeOH by heating, the solution was concentrated. To the residue, 1.66 L of MeCN, 5.72 mL of AcOH (0.1 eq.) and 82.6 g of (S)-2-Amino-propan-1-ol (1.1 eq.) were added and the mixture was heated to 70° C., stirred at 70° C. for 4 h and concentrated. To the residue, 1.67 L of 2-propanol was added and the mixture was concentrated (twice). After cooling of the residue, filtration, washing with 500 mL of cold 2-propanol and drying provided 167 g of compound 14 (52% yield) as a crystal.

$^1$H NMR (300 MHz, CDCl$_3$) δ 7.61-7.55 (m, 2H), 7.40-7.20 (m, 4H), 6.53 (d, J=7.2, 1 H), 5.46 (d, J=10.5 Hz, 1H), 5.23 (d, J=10.2 Hz, 1H), 5.20 (dd, J=3.9, 9.6 Hz, 1H), 4.46-4.34 (m, 1H), 4.31 (dd, J=6.6, 8.7 Hz, 1H), 4.14 (dd, J=3.9, 12.3 Hz, 1H), 3.79 (dd, J=9.9, 12.3 Hz, 1H), 3.62 (dd, J=6.9, 8.7 Hz, 1H), 1.38 (d, J=6.3 Hz, 3H).

Example Ab

To slurry of 156 g of compound 14 (1.0 eq.) in 780 mL of NMP was added 93.6 g of NBS (1.1 eq.) and the mixture was stirred at room temperature for 2.5 h. The reaction mixture was added to 3.12 L of H$_2$O. Filtration, washing with 8.0 L of H$_2$O and drying provided 163 g of compound 15 (84% yield) as a crystal.

$^1$H NMR (300 MHz, DMSO-d$_6$) δ 8.37 (s, 1H), 7.55-7.50 (m, 2H), 7.42-7.25 (m, 3H), 5.34 (dd, J=3.6, 9.9 Hz, 1H), 5.18 (d, J=10.8 Hz, 1H), 5.03 (d, J=10.5 Hz, 1H), 4.53 (dd, J=3.6, 12.0 Hz, 1H), 4.40-4.20 (m, 2H), 3.99 (dd, J=9.9, 11.7 Hz, 1H), 3.64 (dd, J=5.7, 8.1 Hz, 1H), 1.27 (d, J=6.3 Hz, 3H).

Example Ac

Under carbon mono-oxide atmosphere, a mixture of 163 g of compound 15 (1.0 eq.), 163 mL of i-Pr$_2$NEt (2.5 eq.), 68.4 mL of 2,4-difluorobenzylamine (1.5 eq.) and 22.5 g of Pd(PPh$_3$)$_4$ (0.05 eq.) in 816 mL of DMSO was stirred at 90° C. for 7 h. After cooling, removal of precipitate, washing with 50 mL of DMSO and addition of 11.3 g of Pd(PPh$_3$)$_4$ (0.025 eq.), the reaction mixture was stirred at 90° C. for 2 h under carbon mono-oxide atmosphere again. After cooling, removal of precipitate and addition of 2.0 L of AcOEt and 2.0 L of H$_2$O, the organic layer was washed with 1.0 L of 1N HClaq. and 1.0 L of H$_2$O (twice) and the aqueous layer was extracted with 1.0 L of AcOEt. The organic layers were combined and concentrated. Silica gel column chromatography of the residue provided 184 g of compound 16 (96% yield) as foam.

$^1$H NMR (300 MHz, CDCl$_3$) δ 10.38 (t, J=6.3 Hz, 1H), 8.39 (s, 1H), 7.75-7.25 (m, 7H), 6.90-6.70 (m, 2H), 5.43 (d, J=10.2 Hz, 1H), 5.24 (d, J=10.2 Hz, 1H), 5.19 (dd, J=3.9, 9.9

Hz, 1H), 4.63 (d, J=6.0 Hz, 2H), 4.50-4.25 (m, 3H), 3.86 (dd, J=9.9, 12.3 Hz, 1H), 3.66 (dd, J=6.9, 8.4 Hz, 1H), 1.39 (d, J=6.0 Hz, 3H).

Example Ad

Under hydrogen atmosphere, a mixture of 184 g of compound 16 (1.0 eq.) and 36.8 g of 10% Pd—C in 3.31 L of THF and 0.37 L of MeOH was stirred for 3 h. After filtration of precipitate (Pd—C), washing with THF/MeOH (9/1) and addition of 36.8 g of 10% Pd—C, the mixture was stirred for 20 min under hydrogen atmosphere. After filtration of precipitate (Pd—C) and washing with THF/MeOH (9/1), the filtrate was concentrated. After 200 mL of AcOEt was added to the residue, filtration afforded crude solid of compound 17. The precipitates were combined and extracted with 4.0 L of CHCl₃/MeOH (5/1). After concentration of the CHCl₃/MeOH solution and addition of 250 mL of AcOEt to the residue, filtration afforded crude solid of compound 17. The crude solids were combined and dissolved in 8.2 L of MeCN/H₂O (9/1) by heating. After filtration, the filtrate was concentrated. To the residue, 1.5 L of EtOH was added and the mixture was concentrated (three times). After cooling of the residue, filtration and drying provided 132 g of compound 17 (88% yield) as a crystal.

¹H NMR (300 MHz, DMSO-d₆) δ 11.47 (brs, 1H), 10.31 (t, J=6.0 Hz, 1H), 8.46 (s, 1H), 7.40 (td, J=8.6, 6.9 Hz, 1H), 7.24 (ddd, J=2.6, 9.4, 10.6, 1H), 7.11-7.01 (m, 1H), 5.39 (dd, J=4.1, 10.4 Hz, 1H), 4.89 (dd, J=4.2, 12.3 Hz, 1H), 4.55 (d, J=6.0 Hz, 2H), 4.40 (dd, J=6.8, 8.6 Hz, 1H), 4.36-4.22 (m, 1H), 4.00 (dd, J=10.2, 12.3. Hz, 1H), 3.67 (dd, J=6.7, 8.6 Hz, 1H), 1.34 (d, J=6.3 Hz, 3H).

Example Ae

After dissolution of 16.0 g of compound 17 (1.0 eq.) in 2.56 L of EtOH and 0.64 L of H₂O by heating, followed by filtration, 39 mL of 1N NaOHaq. (1.0 eq.) was added to the solution at 75° C. The solution was gradually cooled to room temperature. Filtration, washing with 80 mL of EtOH and drying provided 13.5 g of compound 18 (80% yield) as a crystal.

¹H NMR (300 MHz, DMSO-d₆) δ 10.73 (t, J=6.0 Hz, 1H), 7.89 (s, 1H), 7.40-7.30 (m, 1H), 7.25-7.16 (m, 1H), 7.07-6.98 (m, 1H), 5.21 (dd, J=3.8, 10.0 Hz, 1H), 4.58 (dd, J=3.8, 12.1 Hz, 1H), 4.51 (d, J=5.4 Hz, 2H), 4.30-4.20 (m, 2H), 3.75 (dd, J=10.0, 12.1 Hz, 1H), 3.65-3.55 (m, 1H), 1.27 (d, J=6.1 Hz, 3H).

Example B

This Example B utilizes a process to insert a ring nitrogen in place of oxygen in a pyrone ring and create an aldehyde equivalent by an osmium oxidation of a double bond. Thus, this example is not a bromination of the invention.

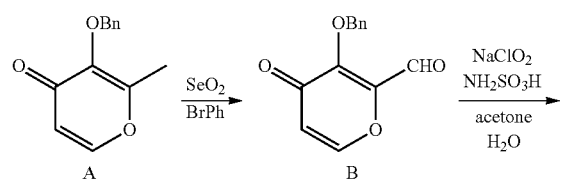

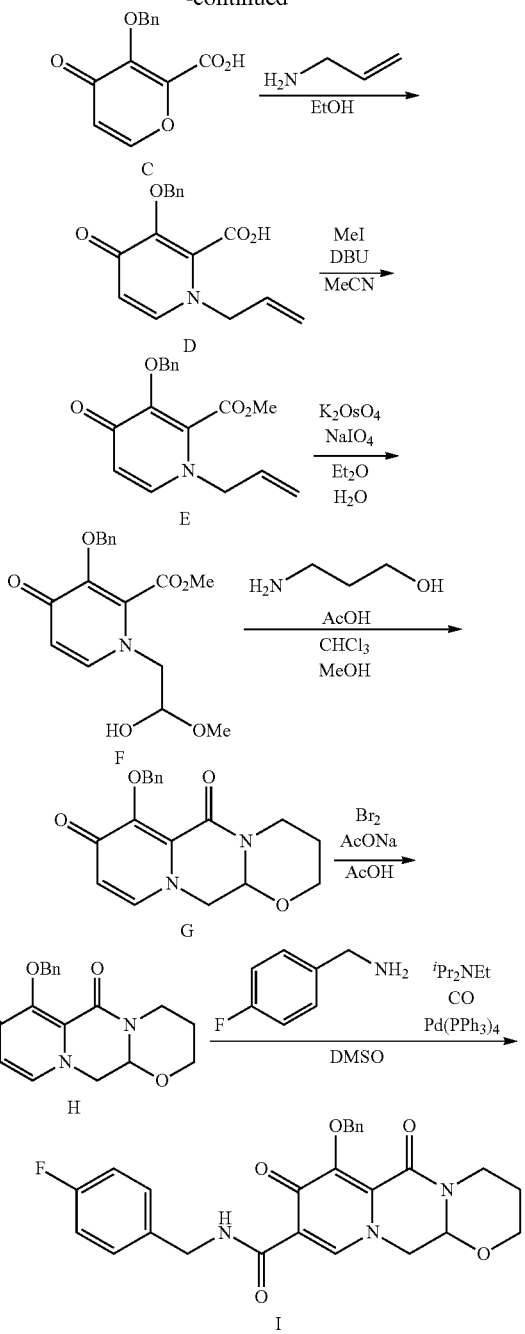

Example Ba

To a bromobenzene (238 ml) solution of compound A (23.8 g, 110 mmol), selene dioxide (24.4 g, 220 mmol) was added. The reaction mixture was stirred for 13 hours at 140° C. with removing water by Dean-Stark trap. Insoluble particles were removed by filtration after cooling, and solvent was evaporated. Toluene was added to the residue and precipitates were filtered off. After concentration in vaccuo, the residue was purified by silica gel column chromatography (hexane/ethyl acetate). Compound B (16.5 g, 65%) was obtained as yellow oil.

¹H-NMR (CDCl₃) δ: 5.51 (2H, s), 6.50 (1H, d, J=5.4 Hz), 7.36 (5H, s), 7.75 (1H, d, J=5.4 Hz), 9.88 (1H, s).

Example Bb

To an ice cooled aqueous (465 ml) solution of sodium chlorite (38.4 g, 424 mmol) and sulfamic acid (54.9 g, 566 mmol), acetone (465 ml) solution of compound B (46.5 g, 202 mmol) was added and the mixture was stirred for 40 minutes at room temperature. After removing acetone in vaccuo, precipitates were collected by filtration and washed with cold water. Compound C (42.8 g, 86%) was obtained as colorless crystal.
$^1$H-NMR (DMSO-d$_6$) δ: 5.12 (2H, s), 6.54 (1H, d, J=5.6 Hz), 7.33-7.46 (5H, m), 8.20 (1H, d, J=5.6 Hz).

Example Bc

An ethanol (17 ml) solution of allylamine (13.2 g 231 mmol) was added to an ethanol (69 ml) suspension of compound C (17.2 g, 70 mmol), then the mixture was stirred for 4.5 hours at 50° C. and for 3 hours at 75° C. To the cooled reaction mixture, 2N hydrochloric acid and ice were added and precipitates were collected by filtration. Compound D was obtained as colorless crystal.
$^1$H-NMR (CDCl$_3$) δ: 4.37 (2H, brs), 4.95 (2H, s), 5.26-5.39 (2H, m), 5.81-5.94 (1H, m), 6.32 (1H, dd, J=0.8, 7.2 Hz), 7.29-7.37 (3H, m), 7.48-7.51 (2H, m), 7.99 (1H, dd, J=0.8, 7.6 Hz), 8.11 (1H, brs).

Example Bd

To an acetonitrile (146 ml) suspension of compound D (14.6 g, 51 mmol), 1,8-diazabicyco[5.4.0]undec-7-ene (15.5 g, 102 mmol) and methyl iodide (18.2 g, 128 mmol) were added and the mixture was stirred for 15 hours at room temperature. After evaporating solvent, the residue was purified by silica gel column chromatography (chloroform/methanol). Compound E (14.2 g, 93%) was obtained as colorless solid.
$^1$H-NMR (CDCl$_3$) δ: 3.75 (3H, s), 4.40 (2H, d, J=5.7 Hz), 5.16-5.35 (2H, m), 5.29 (2H, s), 5.81-5.94 (1H, m), 6.62 (1H, d, J=7.5 Hz), 7.27-7.42 (6H, m).

Example Be

To a diethyl ether (390 ml) solution of compound E (13.3 g, 44 mmol), potassium osmate(VI) dihydrate (1.62 g, 4.4 mmol) and sodium metaperiodate (28.1 g, 132 mmol) were added. The mixture was stirred for 2.5 hours at room temperature and precipitates were collected by filtration. Collected solid was dissolved in chloroform-methanol and insoluble particles were filtered off. Concentration in vaccuo gave crude product of compound F (14.3 g). 1H NMR (DMSO-d6) δ: 3.23 (3H, s), 3.82 (3H, s), 3.87 (2H, t, J=4.4 Hz), 4.62 (1H, dd, J=11.7, 4.8 Hz), 5.11 (2H, s), 6.31 (1H, d, J=7.5 Hz), 6.78 (1H, d, J=6.6 Hz), 7.33-7.40 (5H, m), 7.64 (1H, d, J=7.5 Hz).

Example Bf

To chloroform (108 ml) and methanol (12 ml) solution of compound F (11.7 g, crude product), 3-aminopropanol (2.77 g, 36.9 mmol), and acetic acid (1.2 ml) were added and the mixture was stirred for 90 minutes at 70° C. After concentrating in vaccuo, the residue was purified by silica gel column chromatography (chloroform/methanol). Compound G (8.48 g, 72% for 2 steps) was obtained as colorless crystal.
$^1$H-NMR (CDCl$_3$) δ: 1.54-1.64 (1H, m), 1.85-2.01 (1H, m), 3.00 (1H, dt, J=3.6, 12.9 Hz), 3.74 (1H, dt, J=2.7, 12.3 Hz), 3.93 (1H, dd, J=5.1, 13.5 Hz), 4.07-4.21 (2H, m), 4.63-4.69 (1H, m), 4.94 (1H, t, J=4.8 Hz), 5.25 (2H, dd, J=10.2, 24.6 Hz), 6.56 (1H, d, J=7.5 Hz), 7.22-7.38 (5H, m), 7.63-7.66 (2H, m).

Example Bg

To acetic acid (93 ml) solution of compound G (6.1 g, 18.7 mmol), acetic acid (31 ml) solution of bromine (1.44 ml, 28.0 mmol) was added dropwisely during 15 minutes. The mixture was stirred for 3 hours at room temperature. After addition of 5% aqueous sodium hydrogen sulfite (8 ml), 2N sodium hydroxide (500 ml) was added dropwisely during 20 minutes. Precipitates were collected by filtration and washed with mixture of dichloromethane and diisopropyl ether. Compound H (6.02 g, 79%) was obtained as colorless crystal.
$^1$H-NMR (DMSO-d$_6$) δ: 1.55-1.74 (2H, m), 3.12 (1H, dt, J=3.0, 12.3 Hz), 3.84 (1H, dt, J=2.7, 11.7 Hz), 4.00-4.05 (1H, m), 4.20-4.26 (1H, m), 4.40-4.46 (2H, m), 5.03 (2H, s), 5.15-5.17 (1H, m), 7.31-7.40 (3H, m), 7.56-7.58 (2H, m), 8.39 (1H, s).

Example Bh

To dimethyl sulfoxide (1.42 ml) solution of compound H (71 mg, 0.175 mmol) and tetrakis(triphenylphosphine)palladium(0) (25 mg, 0.035 mmol), 4-fluorobenzyl amine (0.06 ml, 0.525 mmol) and diisopropyl amine (0.15 ml, 0.875 mmol) were added, then the mixture was stirred under carbon monoxide atmosphere for 5 hours at 80° C. After cooling, saturated aqueous ammonium chloride was added and the mixture was extracted with ethyl acetate. The extract was washed with water and dried with anhydrous sodium sulfate. Solvent was removed in vaccuo and the residue was purified with silica gel column chromatography (ethyl acetate/methanol). Compound I (74.5 mg, 89%) was obtained as colorless crystal.
$^1$H-NMR (DMSO-d$_6$) δ: 1.58-1.74 (2H, m), 3.10-3.18 (1H, m), 3.80-3.88 (1H, m), 4.02-4.07 (1H, m), 4.43-4.59 (5H, m), 5.05 (2H, s), 5.20 (1H, t, J=3.9 Hz), 7.13-7.19 (2H, m), 7.32-7.40 (5H, m), 7.56-7.59 (2H, m), 8.61 (1H, s).

Example C

Synthesis of methyl 5-bromo-1-[2-hydroxy-2-(methyloxy)ethyl]-4-oxo-3-[(phenylmethyl)oxy]-1,4-dihydro-2-pyridinecarboxylate (in equilibrium with the corresponding aldehyde)

This Example C shows a refunctionalization of a compound 6 as shown above in Example 1 (of formula (VI)), including a bromination at the Fe position, to yield final products 20 and 21 (of formula (I)). Such compounds with Br at the Fe position can be reacted as in Examples 1 and 2 to add the R$^2$—X—NR'—C(O)— sidechain.

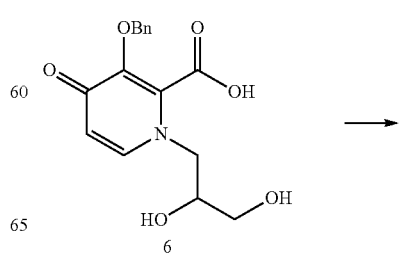

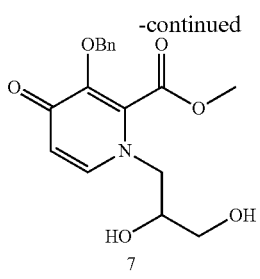

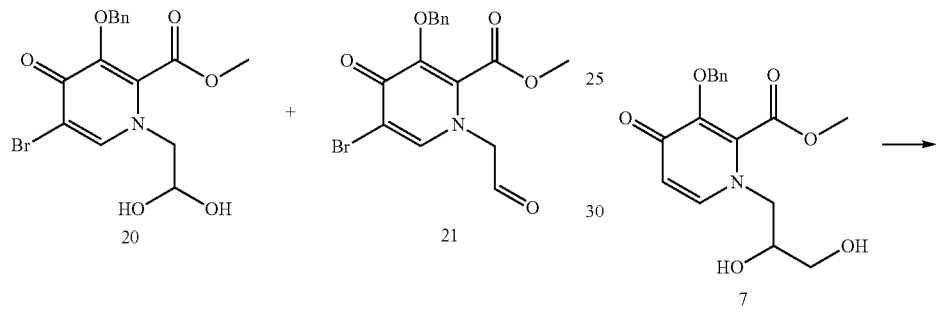

Example Ca

Methyl 1-(2,3-dihydroxypropyl)-4-oxo-3-[(phenylmethyl)oxy]-1,4-dihydro-2-pyridinecarboxylate

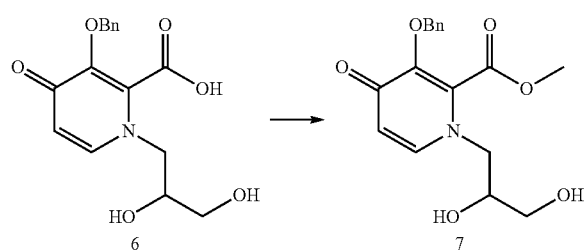 [SMILES: O=C(O)c1c(OCc2ccccc2)c(=O)ccn1CC(O)CO ; COC(=O)c1c(OCc2ccccc2)c(=O)ccn1CC(O)CO]

A reactor was charged with 1-(2,3-dihydroxypropyl)-4-oxo-3-[(phenylmethyl)oxy]-1,4-dihydro-2-pyridinecarboxylic acid 6 (4.302 kg, 13.47 mol) followed by charging with NaHCO$_3$ (1.69 kg, 20.09 mol) and 242 g of deionized water. To this was added 21.4 kg of NMP and the mixture was stirred and temperature brought to 28-35° C. Dimethyl sulfate (2.34 kg, 18.30 mol) was added dropwise via an addition funnel to the reaction mixture over 1-3 hours keeping the temperature at 28-33° C. The slurry was agitated at this temperature for 14 h. When deemed complete, the reaction mixture was cooled to 5° C. or below and the mixture was neutralized to pH 6 by the addition of HCl (561 mL of conc HCl in 2806 g of deionized water). The reaction vessel was slowly charged with cold 20% brine solution composed of 8.7 kg NaCl, 20 kg of deionized water and 14.8 kg of ice at a maximum temperature of 10° C. The mixture was agitated at 0-10° C. for 2.5 h. The slurry was filtered under vacuum and the cake washed with 15 kg of deionized water two times. The wet solid product was dried at 45-55° C. under vacuum until constant weight was obtained. The desired product methyl 1-(2,3-dihydroxypropyl)-4-oxo-3-[(phenylmethyl)oxy]-1,4-dihydro-2-pyridinecarboxylate 7 was obtained as a light yellow solid (3.77 kg, 99.42% purity by HPLC, 84%). $^1$H NMR (300 MHz, DMSO-d$_6$) δ 7.60 (d, J=7.5 Hz, 1H), 7.36 (m, 5H), 6.28 (d, J=7.5 Hz, 1H), 5.23 (d, J=5.4 Hz, 1H), 5.10 (Abq, J=10.8 Hz, 2H), 4.85 (m, 1H), 3.98 (dd, J=14.3, 2.4 Hz, 1H), 3.79 (s, 3H), 3.70 (dd, J=14.3, 9.0 Hz, 1H), 3.58 (m, 1H), 3.23 (m, 1H).

Example Cb

Methyl 5-bromo-1-(2,3-dihydroxypropyl)-4-oxo-3-[(phenylmethyl)oxy]-1,4-dihydro-2-pyridinecarboxylate

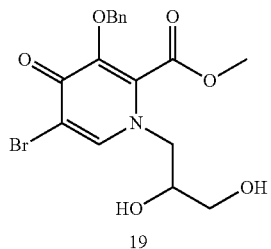

A reactor was charged with (3.759 kg, 11.27 mol) of methyl 1-(2,3-dihydroxypropyl)-4-oxo-3-[(phenylmethyl)oxy]-1,4-dihydro-2-pyridinecarboxylate 7 and 18.8 L of DMF. To this agitated mixture at 18-20° C. was added N-bromosuccinimide (2.220 kg, 12.47 mol) over 20 minutes via a powder funnel. The resultant mixture was stirred at rt for 16 h. At this time less than 1% of starting material was present by HPLC. The mixture was worked up in half batches by cooling to 10° C. and added an ice/water mixture (12 kg ice in 35 kg deionized water) and the mixture was agitated, then filtered. This was repeated for the second half of the batch. The combined filter cake was washed with 14 L of water and dried in a vacuum oven to provide 4.033 kg of methyl 5-bromo-1-(2,3-dihydroxypropyl)-4-oxo-3-[(phenylmethyl)oxy]-1,4-dihydro-2-pyridinecarboxylate 19 (91.6%) as an off-white powder of 99.2% HPLC purity. $^1$H NMR (300 MHz, Methanol-d$_4$) δ 8.21 (s, 1H), 7.41-7.33 (m, 5H), 5.16 (s, 2H), 4.17 (dd, J=14.3, 2.4 Hz, 1H), 3.90 (dd, J=14.3, 9.0 Hz, 1H), 3.81 (s, 3H), 3.78 (m, 1), 3.52 (dd, J=11.3, 4.8 Hz, 1H), 3.41 (dd, J=11.3, 6.3 Hz, 1H).

Example Cc

Methyl 5-bromo-1-[2-hydroxy-2-(methyloxy)ethyl]-4-oxo-3-[(phenylmethyl)oxy]-1,4-dihydro-2-pyridinecarboxylate (in equilibrium with the corresponding aldehyde)

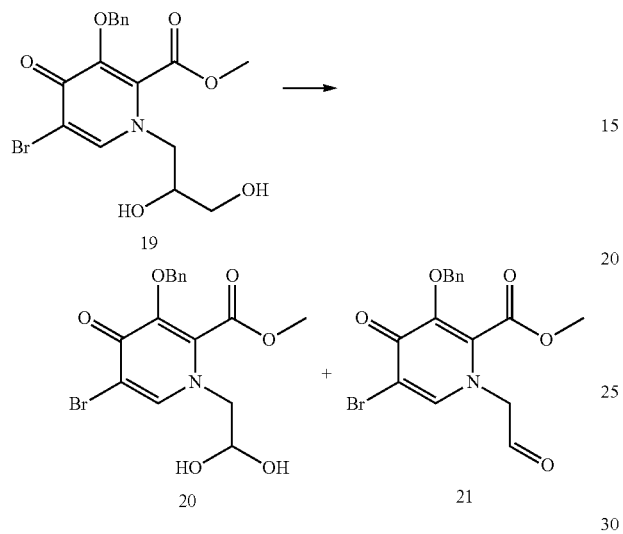

A reactor was charged with sodium periodate (1.67 kg, 7.8 mol) and 44 L of deionized water. To the agitated mixture was added 8.5 kg of ice. This was stirred until all the ice melted and the mixture temperature was 1.4° C. To this was added methyl 5-bromo-1-(2,3-dihydroxypropyl)-4-oxo-3-[(phenylmethyl)oxy]-1,4-dihydro-2-pyridinecarboxylate 19 (2.73 kg, 6.62 mol) via a powder addition funnel. The mixture was allowed to warm to rt and the slurry was stirred for 16 h. A sample was monitored by $^1$H NMR and showed the disappearance of starting material. The mixture was filtered and the cake washed with 20 kg of deionized water. This was repeated until a negative starch/iodide paper result was obtained (4×20 L washes). The solids were dried in a vacuum oven at 45-55° C. to provide methyl 5-bromo-1-(2,2-dihydroxyethyl)-4-oxo-3-[(phenylmethyl)oxy]-1,4-dihydro-2-pyridinecarboxylate 20 (2.176 kg, 88%) as a mixture with the corresponding aldehyde form 21. Purity was determined to be 99.5% by HPLC. $^1$H NMR (300 MHz, acetone-$d_6$) δ 8.12 (s, 1H), 7.49-7.30 (m, 5H), 5.56 (dd, J=6.0, 2.4 Hz, 1H), 5.23 (m, 1H), 5.20 (s, 2H), 3.97 (d, J=5.1 Hz, 2H), 3.87 (s, 3H).

Example 2

Methyl 5-({[(2,4-difluorophenyl)methyl]amino}carbonyl)-1-[2-hydroxy-2-(methyloxy)ethyl]-4-oxo-3-[(phenylmethyl)oxy]-1,4-dihydro-2-pyridinecarboxylate (in equilibrium with the corresponding aldehyde)

This Example shows a reaction of a compound 5 of formula (II) with one of (III) in step i) and a refunctionalization step ii) of compounds of formula (V) (compounds 22, 23, 24 and 25) in producing compounds of formula (I).

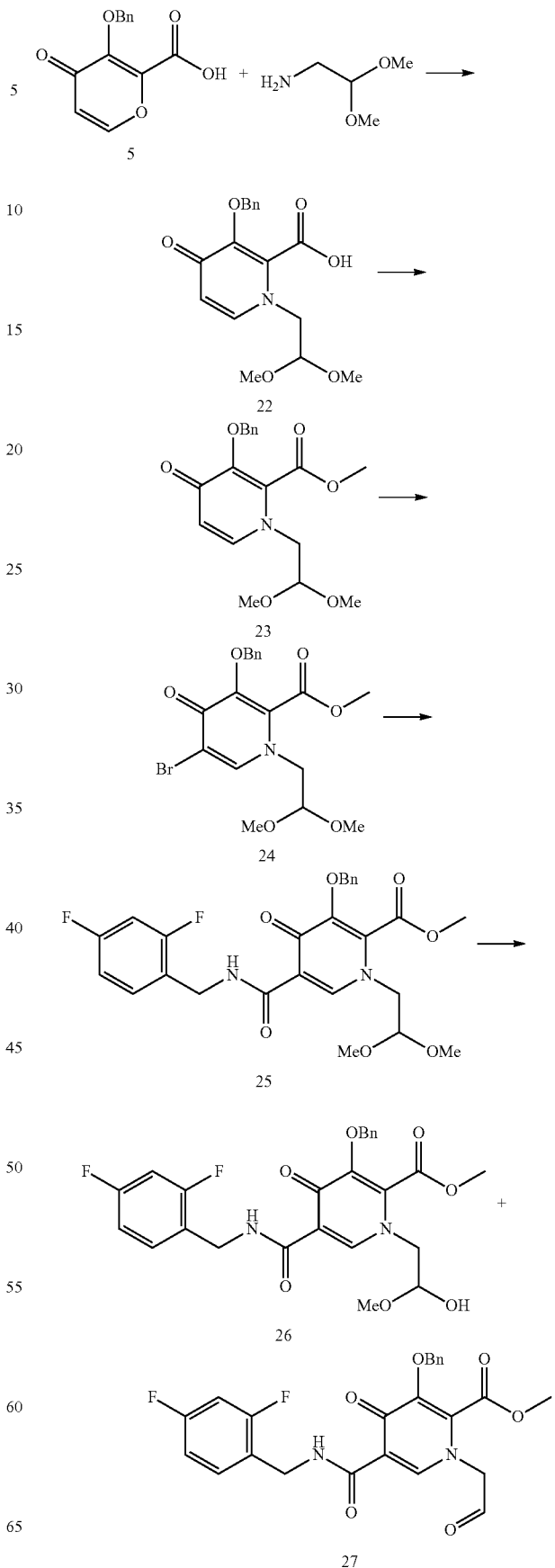

Example 2a

1-[2,2-Bis(methyloxy)ethyl]-4-oxo-3-[(phenylmethyl)oxy]-1,4-dihydro-2-pyridinecarboxylic acid

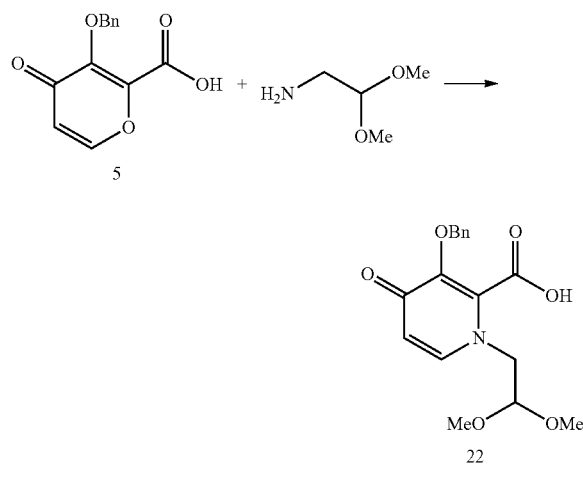

To a flask (1 L) charged with 500 mL of anhydrous ethanol was added 49.2 g (0.2 mol) of 4-oxo-3-[(phenylmethyl)oxy]-4H-pyran-2-carboxylic acid 5. The suspension was slowly heated to 55~60° C. before addition of 2-amino-acetaldehyde-dimethylacetal (84.1 g, 0.8 mole). The reaction was then brought up to 65° C. and further stirred for 18 hours. The solvent was removed under reduced pressure to produce 1-[2,2-Bis(methyloxy)ethyl]-4-oxo-3-[(phenylmethyl)oxy]-1,4-dihydro-2-pyridinecarboxylic acid 22 (crude) as brown oil, which was used for the next step directly.

Example 2b

Methyl 1-[2,2-bis(methyloxy)ethyl]-4-oxo-3-[(phenylmethyl)oxy]-1,4-dihydro-2-pyridinecarboxylate

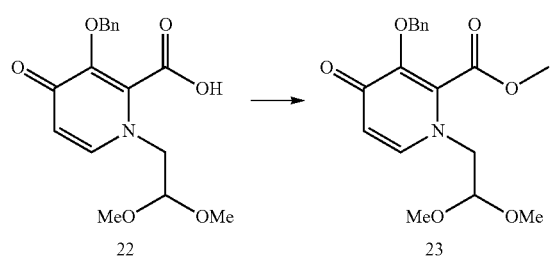 [SMILES: COC(Cn1ccc(=O)c(OCc2ccccc2)c1C(=O)O)OC ; COC(=O)c1c(OCc2ccccc2)c(=O)ccn1CC(OC)OC]

Crude 1-[2,2-bis(methyloxy)ethyl]-4-oxo-3-[(phenylmethyl)oxy]-1,4-dihydro-2-pyridinecarboxylic acid 22 obtained as above was dissolved in DMF (500 mL). To this solution was added NaHCO$_3$(50.5 g, 0.6 mole). The suspension was stirred vigorously with a mechanic stirrer while CH$_3$I in TBME (2.0M, 300 mL) was introduced by addition funnel over 30 minutes. After addition, the reaction was stirred overnight at room temperature. The reaction mixture was then diluted with EtOAc (~1.5 L) and washed with water and brine. The organic layer was dried over anhydrous Na$_2$SO$_4$. Evaporation of solvents gave methyl 1-[2,2-bis(methyloxy)ethyl]-4-oxo-3-[(phenylmethyl)oxy]-1,4-dihydro-2-pyridinecarboxylate 23 as brown oil, which was used directly for the next step.

Example 2c

Methyl 1-[2,2-bis(methyloxy)ethyl]-5-bromo-4-oxo-3-[(phenylmethyl)oxy]-1,4-dihydro-2-pyridinecarboxylate

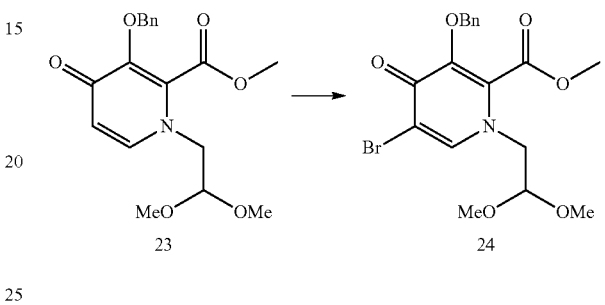

A 2 L flask equipped with a mechanic stirrer were charged with methyl 1-[2,2-bis(methyloxy)ethyl]-4-oxo-3-[(phenylmethyl)oxy]-1,4-dihydro-2-pyridinecarboxylate 23 as obtained above and 500 mL of dichloromethane. To this flask was added NBS (30 g, 0.17 mole) portion-wise. The reaction was stirred at room temperature until its completion (monitored by TLC, ~6 hours). The mixture was then diluted with dichloromethane and washed with NaHCO$_3$ (ss). The organic phase was dried over Na$_2$SO$_4$ before evaporation of the solvents. The crude product was purified by column chromatography (silica gel, EtOH/DCM: 0-40%) to afford methyl 1-[2,2-bis(methyloxy)ethyl]-5-bromo-4-oxo-3-[(phenylmethyl)oxy]-1,4-dihydro-2-pyridinecarboxylate 24 as a light brown solid (50 g, 60% over three steps). $^1$H NMR (400 MHz, CHLOROFORM-d) δ ppm 7.7 (s, 1H), 7.4 (m, 2H), 7.3 (d, J=7.9 Hz, 3H), 5.3 (s, 2H), 4.4 (s, 1H), 3.8 (d, J=4.8 Hz, 2H), 3.8 (s, 3H), 3.4 (s, 6H). LC-MS (M+H$^+$): calcd 426. obsd 426.

Example 2d

Methyl 1-[2,2-bis(methyloxy)ethyl]-5-({[(2,4-difluorophenyl)methyl]amino}carbonyl)-4-oxo-3-[(phenylmethyl)oxy]-1,4-dihydro-2-pyridinecarboxylate

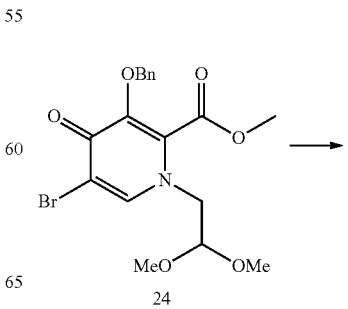

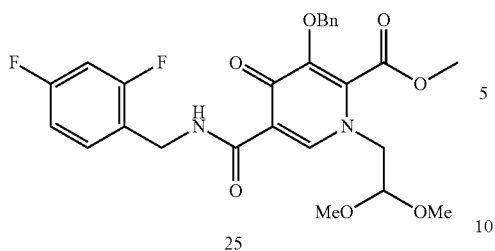

25

A pressure vessel was charged with methyl 1-[2,2-bis(methyloxy)ethyl]-5-bromo-4-oxo-3-[(phenylmethyl)oxy]-1,4-dihydro-2-pyridinecarboxylate 24 (6.4 g, 15 mmol), 2,4-difluorobenzylamine (3.2 g, 22.5 mmol), $K_3PO_4$ (9.45 g, 45 mmol), $Pd(OCOCF_3)_2$ (398 mg, 1.2 mmol), Xantphos (694 mg, 1.2 mmol) and toluene (200 mL). The mixture was purged by CO (4×) before being heated to 100° C. for 22 hours under CO atmosphere (60 psi). After cooled down to the room temperature, the solids were filtered off through celite and washed with EtOAc. The filtrate was concentrated and the residual was purified by column chromatography (silica gel, EtOAc/hexane 0-80%) to afford methyl 1-[2,2-bis(methyloxy)ethyl]-5-({[(2,4-difluorophenyl)methyl]amino}carbonyl)-4-oxo-3-[(phenylmethyl)oxy]-1,4-dihydro-2-pyridinecarboxylate 25 as a light brown oil (4.7 g, 61%).

1H NMR (400 MHz, CHLOROFORM-d) δ ppm 10.4 (m, 1H), 8.4 (s, 1H), 7.4 (m, 6H), 6.8 (d, J=9.3 Hz, 2H), 5.3 (s, 2H), 4.6 (d, J=5.7 Hz, 2H), 4.5 (s, 1H), 4.0 (d, J=4.8 Hz, 2H), 3.8 (s, 3H), 3.4 (s, 6H). LC-MS (M+H$^+$): calcd 517. obsd 517.

Example 2e

Methyl 5-({[(2,4-difluorophenyl)methyl]amino}carbonyl)-1-[2-hydroxy-2-(methyloxy)ethyl]-4-oxo-3-[(phenylmethyl)oxy]-1,4-dihydro-2-pyridinecarboxylate (in equilibrium with the corresponding aldehyde)

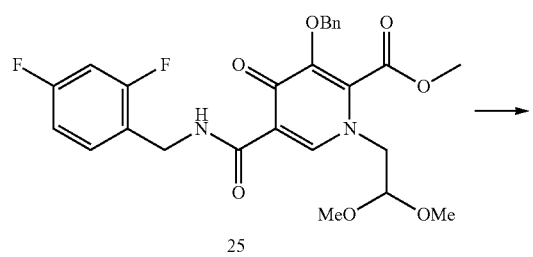

+

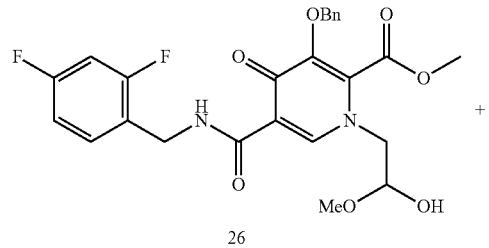

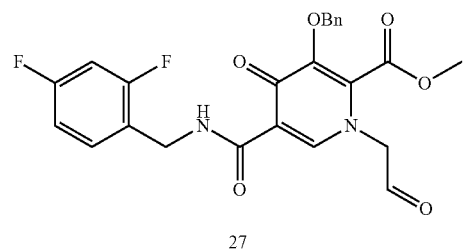

27

Methyl 1-[2,2-bis(methyloxy)ethyl]-5-({[(2,4-difluorophenyl)methyl]amino}carbonyl)-4-oxo-3-[(phenylmethyl)oxy]-1,4-dihydro-2-pyridinecarboxylate 25 (11.6 g) was treated with 90% formic acid (250 mL) at 40° C. for ~12 hours (monitored by LC-MS). After the solvents were evaporated at <40° C., the residue was re-dissolved in EtOAc (~1 L) and the resulting solution was washed with $NaHCO_3$ and brine. The organic phase was then dried over $Na_2SO_4$. After evaporation of solvents, the titled compounds 26 and 27 were obtained as an approximate 80/20 equilibrium mixture (10.57 g). $^1$H NMR (400 MHz, DMSO-d$_6$) δ ppm 10.3 (m, 1H), 9.47 (s, aldehyde-H. ~0.2H)), 8.4 (m, 1H), 7.3 (s, 6H), 7.2 (m, 1H), 7.0 (m, 1H), 6.3 (m, 2H), 5.1 (s, 3H), 4.9 (m, 1H), 4.5 (m, 3H), 3.9 (m, 2H), 3.8 (s, 3H). LC-MS, for 26 (M+H$^+$), calcd 503. obsd 503. for 27 (M+H$_2$O+H$^+$), calcd 489, obsd 489.

Example CC (4aS,13aR)—N-[(2,4-Difluorophenyl)methyl]-10-hydroxy-9,11-dioxo-2,3,4a,5,9,11,13,13a-octahydro-1H-pyrido[1,2-a]pyrrolo[1',2':3,4]imidazo[1,2-d]pyrazine-8-carboxamide

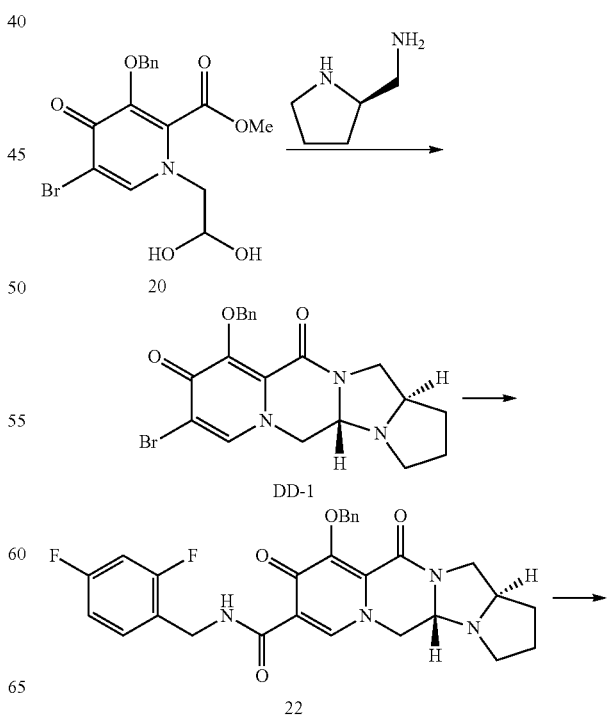

-continued

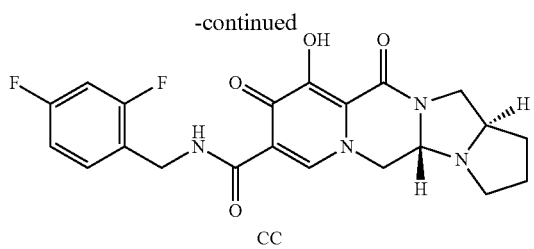

CC

Example CCa (4aS,13aR)-8-Bromo-10-[(phenylmethyl)oxy]-2,3, 4a,5,13,13a-hexahydro-1H-pyrido[1,2-a]pyrrolo[1', 2':3,4]imidazo[1,2-d]pyrazine-9,11-dione (DD)

A reactor was charged with [(2R)-2-pyrrolidinylmethyl] amine (0.75 kg) and 4.6 L of DMF was added followed by 0.45 kg of glacial acetic acid. Acetonitrile (41.4 L) was then added and the mixture was agitated for 15 minutes. To the reaction mixture was added methyl 5-bromo-1-(2,2-dihydroxyethyl)-4-oxo-3-[(phenylmethyl)oxy]-1,4-dihydro-2-pyridinecarboxylate (2.30 kg). After stirring for 20 minutes at ambient temperature, the mixture was heated at 75-85° C. until the bromide starting material was consumed by HPLC analysis (about 6 hrs). Upon completion, the mixture was cooled until the reflux subsided and then charged with 6.9 L of methanol and the mixture was heated at reflux for about 45 minutes then cooled to 15° C. and filtered and dried to provide (4aS,13aR)-8-bromo-10-[(phenylmethyl)oxy]-2,3,4a,5,13, 13a-hexahydro-1H-pyrido[1,2-a]pyrrolo[1',2':3,4]imidazo [1,2-d]pyrazine-9,11-dione (1.93 kg, 78%) as a white solid). $^1$H NMR (300 MHz, DMSO-$d_6$) δ ppm 8.65 (m, 1H), 7.54 (m, 2H), 7.33 (m, 3H), 5.15 (d, 1H), 4.99 (d, 1H), 4.60 (m, 1H), 4.36 (m, 1H), 4.03 (m, 1H), 3.90 (m, 1H), 3.65 (m, 1H), 3.06-2.84 (m, 3H), 1.92-1.60 (m, 4H).

Example CCb (4aS,13aR)—N-[(2,4-Difluorophenyl)methyl]-9,11-dioxo-10-[(phenylmethyl)oxy]-2,3,4a,5,9,11,13,13a-octahydro-1H-pyrido[1,2-a]pyrrolo[1',2':3,4]imidazo [1,2-d]pyrazine-8-carboxamide A reaction vessel was charged with (4aS,13aR)-8-bromo-10-[(phenylmethyl)oxy]-2,3,4a,5,13,13a-hexahydro-1H-pyrido[1,2-a]pyrrolo[1',2':3,4]imidazo[1,2-d]pyrazine-9,11-dione (1.4 kg), 2,4-difluorobenzylamine (705 g), Hunigs base (1.4 L), dppf (60 g) and DMSO (12 L). The mixture was degassed with high purity nitrogen 4 times. To this mixture was added palladium (II) trifluoroacetate (18 g) in DMSO (2 L). The mixture was again degassed 3 times with high purity nitrogen and then purged with CO 3 times and left under a 45 psi atmosphere of CO. The mixture was heated at 80° C. under 45 psi CO until the reaction appeared complete by HPLC (24 hrs). The mixture was cooled to rt and slowly transferred to an ice slurry of ammonium chloride. The mixture was filtered and washed with water and isopropanol. The residue was recrystallized from isopropanol to provide (4aS, 13aR)—N-[(2,4-Difluorophenyl)methyl]-9,11-dioxo-10-[(phenylmethyl)oxy]-2,3,4a,5,9,11,13,13a-octahydro-1H-pyrido[1,2-a]pyrrolo[1',2':3,4]imidazo[1,2-d]pyrazine-8-carboxamide (952 g, 56%). Recrystallization of the mother liquor from isopropanol produced a second crop of crystals of the desired product in the amount of 327 g (19%). $^1$H NMR (300 MHz, DMSO-$d_6$) δ ppm 10.44 (m, 1H), 8.55 (s, 1H), 7.56-7.07 (m, 8H), 5.18 (d, 1H), 5.03 (d, 1H), 4.62-4.54 (m, 4H), 4.06-3.60 (m, 3H), 3.20-2.80 (m, 3H), 1.93-1.60 (m, 4H).

Example CCc (4aS,13aR)—N-[(2,4-Difluorophenyl)methyl]-10-hydroxy-9,11-dioxo-2,3,4a,5,9,11,13,13a-octahydro-1H-pyrido[1,2-a]pyrrolo[1',2':3,4]imidazo[1,2-d] pyrazine-8-carboxamide A pressure reaction vessel was charged with (4aS,13aR)—N-[(2,4-Difluorophenyl)methyl]-9,11-dioxo-10-[(phenylmethyl)oxy]-2,3,4a,5,9,11,13,13a-octahydro-1H-pyrido[1,2-a]pyrrolo[1',2':3,4]imidazo[1,2-d]pyrazine-8-carboxamide (950 g), 192 g of palladium on carbon (50% wet), ethanol (9.5 L) and concentrated ammonium hydroxide (124 mL). The mixture was degassed with nitrogen 3 times and then placed under 50 psi of hydrogen until the reaction was complete. The mixture was degassed again with nitrogen and then filtered through Celite. The cake was extracted with refluxing dichloromethane and then filtered again. The combined filtrates were concentrated to a small volume (4 L), azeotroped with ethanol (28.5 L) to a final volume of 9 L. The slurry was filtered and washed with ethanol and dried to produce (4aS, 13aR)—N-[(2,4-difluorophenyl)methyl]-10-hydroxy-9,11-dioxo-2,3,4a,5,9,11,13,13a-octahydro-1H-pyrido[1,2-a]pyrrolo[1',2':3,4]imidazo[1,2-d]pyrazine-8-carboxamide (616 g, 78.4%) as a white solid. $^1$H NMR (300 MHz, DMSO-$d_6$) δ ppm 10.37 (m, 1H), 8.42 (s, 1H), 7.41-7.05 (m, 3H), 4.72-4.53 (m, 4H), 4.05 (m, 1H), 3.86 (m, 1H), 3.70 (m, 1H), 3.16 (m, 1H), 2.88 (m, 2H), 1.92-1.60 (m, 4H).

What is claimed is:

1. A process for the preparation of a compound of the following formula (I):

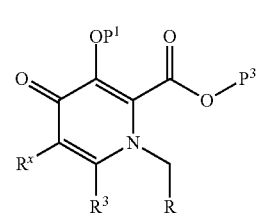

(I)

wherein
R is —CHO, —CH(OH)$_2$ or —CH(OH)(OR$^4$);
P$^1$ is H or a hydroxyl protecting group;
P$^3$ is H or a carboxy protecting group;
R$^3$ is H, halogen, hydroxy, optionally substituted lower alkyl, optionally substituted cycloalkyl, optionally substituted lower alkenyl, optionally substituted lower alkoxy, optionally substituted lower alkenyloxy, optionally substituted aryl, optionally substituted aryloxy, optionally substituted heterocyclic group, optionally substituted heterocycleoxy and optionally substituted amino;
R$^4$ is lower alkyl;
R$^x$ is H, halogen or R$^2$—X—NR$^1$—C(O)—;
R$^2$ is optionally substituted aryl;
X is a single bond, a heteroatom group selected from the group consisting of O, S, SO, SO$_2$, and NH or a lower alkylene or a lower alkenylene wherein each may be intervened by the heteroatom; and
R$^1$ is H or lower alkyl, which comprises the steps of:
i) reacting a compound of formula (II):

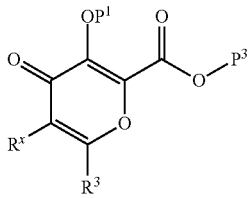

wherein $P^1$, $P^3$, $R^x$ and $R^3$ are defined above;
with an amine of formula (III) or (IV):

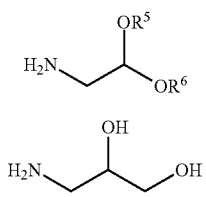

wherein $R^5$ and $R^6$ are independently lower alkyl or $R^5$ and $R^6$ can be alkyl and joined to form a 5-, 6-, or 7-membered ring,
to produce an intermediate of formula (V) or (VI), respectively:

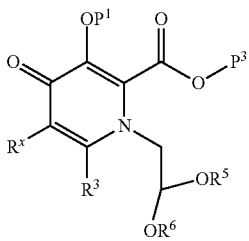

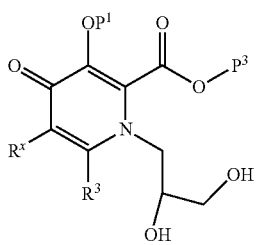

wherein $P^1$, $P^3$, $R^x$, $R^3$, $R^5$ and $R^6$ are defined above; and
ii) refunctionalizing the intermediate of formula (V) or (VI) to produce the compound of formula (I).

2. The process according to claim 1, wherein in the compound of formula (I), $R^x$ is H or Br.

3. The process according to claim 1, wherein in the compound of formula (I), $P^1$ is H or Bn.

4. The process according to claim 1, wherein in the compound of formula (I), $R^3$ is H.

5. The process according to claim 1, wherein in the compound of formula (I), $P^3$ is H or Me.

6. The process according to claim 1, wherein the compound of formula (II) is

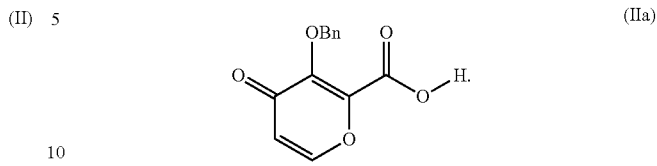

7. The process according to claim 1, wherein the compound of formula (VI) is

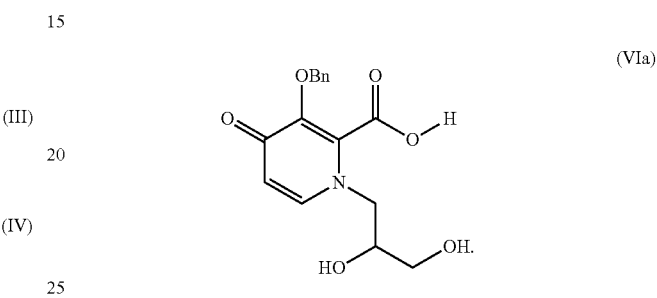

8. The process according to claim 1, wherein the compound of formula (VI) is

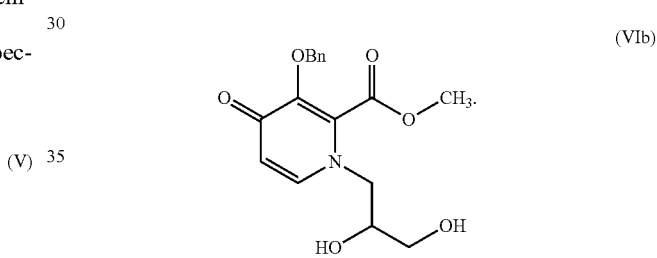

9. The process according to claim 1, wherein the compound of formula (I) is

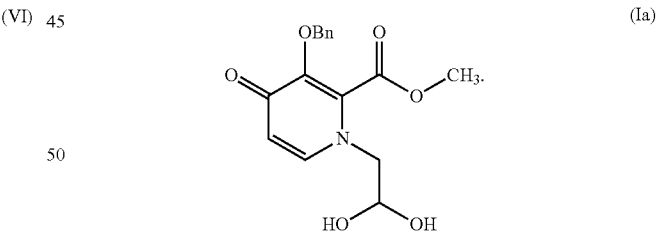

10. The process according to claim 1, wherein the amine is $H_2NCH_2CH_2CH_2OH$.

11. The process according to claim 1, wherein $R^x$ is p-F-phenyl-$CH_2$—NH—C(O)—, $R^3$ is H, $P^1$ is Bn and $P^3$ is a carboxy protecting group.

12. The process according to claim 1, wherein step i) is carried out in EtOH, THF or DMF at a temperature of about 50-150° C.

13. The process according to claim 1, wherein step ii) is carried out using the intermediate of formula (VI) with an oxidizing agent selected from the group consisting of $NaIO_4$, $RuO_4$ and $Pb(OAc)_4$ in a solvent selected from the group consisting of $H_2O$, MeOH and $CH_3CN$.

14. The process according to claim 1, wherein step ii) is carried out using the intermediate of formula (V) with an acid selected from the group consisting of HCl, $CF_3COOH$ and HCOH.

15. The process according to claim 1, wherein step ii) includes refunctionalization of $R^x$ from $R^x$=H to $R^x$=Br.

16. The process according to claim 1, wherein step ii) includes refunctionalization of $R^x$ to $R^x=R^2—X—NR^1—C(O)—$.

17. The process according to claim 1, wherein step ii) includes refunctionalization of $P^3$ from $P^3$=H to $P^3$=Me.

* * * * *